(12) United States Patent
Berezina et al.

(10) Patent No.: US 12,269,784 B2
(45) Date of Patent: Apr. 8, 2025

(54) BIOMASS PRODUCTION

(71) Applicant: NBTECH AB, Järfälla (SE)

(72) Inventors: Nathalie Berezina, Järfälla (SE); Maxim Chapovalov, Järfälla (SE)

(73) Assignee: NBTECH AB, Järfälla (SE)

(*) Notice: Subject to any disclaimer, the term of this patent is extended or adjusted under 35 U.S.C. 154(b) by 0 days.

(21) Appl. No.: 18/567,332

(22) PCT Filed: Jul. 1, 2022

(86) PCT No.: PCT/EP2022/068350
§ 371 (c)(1),
(2) Date: Dec. 5, 2023

(87) PCT Pub. No.: WO2023/275397
PCT Pub. Date: Jan. 5, 2023

(65) Prior Publication Data
US 2024/0261834 A1    Aug. 8, 2024

(30) Foreign Application Priority Data

| Jul. 2, 2021 | (EP) | 21183517 |
| Jul. 2, 2021 | (EP) | 21183520 |
| Nov. 25, 2021 | (EP) | 21210560 |

(51) Int. Cl.

| C05F 17/05 | (2020.01) |
| A01K 67/033 | (2006.01) |
| B09B 3/60 | (2022.01) |
| B09B 101/75 | (2022.01) |
| B09B 101/77 | (2022.01) |
| C05F 9/00 | (2006.01) |
| C08J 11/10 | (2006.01) |

(52) U.S. Cl.
CPC .......... *C05F 17/05* (2020.01); *A01K 67/0339* (2013.01); *B09B 3/60* (2022.01); *C05F 9/00* (2013.01); *C08J 11/105* (2013.01); *B09B 2101/75* (2022.01); *B09B 2101/77* (2022.01); *C08J 2371/02* (2013.01)

(58) Field of Classification Search
CPC .................. B09B 3/60; B09B 2101/75; B09B 2101/77; C05F 17/05; A01K 67/0339; C08J 11/105; C08J 2371/02
USPC .......................................................... 71/14
See application file for complete search history.

(56) References Cited

U.S. PATENT DOCUMENTS

2015/0247018 A1* 9/2015 Yang ............ C08J 11/105
435/71.1

FOREIGN PATENT DOCUMENTS

| CN | 108713530 A | 10/2018 |
| CN | 111671013 A | 9/2020 |
| CN | 113040096 A | 6/2021 |
| EP | 3587557 A1 | 1/2020 |

OTHER PUBLICATIONS

Elliott, et al. Evaluating Bioremediation Potential for Plastic Pollution with Wax Worms, Galleria mellonella (Poster Presentation). WaxWormsPoster_AlexandriaFINAL_resize.pdf, Available: Oct. 11, 2018, pp. 1-2. (Year: 2018).*
Guo et al., "Polyurethane foam induces epigenetic modification of mitochondrial DNA during different metamorphic stages of Tenebrio molitor", Ecotoxicology and Environmental Safety, 2019, 183: 109461, 6 pages.
Peng et al., "Biodegradation of Polyvinyl Chloride (PVC) in Tenebrio molitor (Coleoptera: Tenebrionidae) larvae", Environment International, 2020, 145: 106106, 11 pages.
Peydaei et al., "Mastication of polyolefins alters the microbial composition in Galleria mellonella", Enrvronmental Pollution, Jul. 1, 2021, 280: 116877, 9 pages.
Yang et al., "Biodegradation of polypropylene by yellow mealworms (*Tenebrio molitor*) and superworms (*Zophobas atratus*) via gut-microbe-dependent depolymerization", Science of the Total Environment, Nov. 26, 2020, 756: 144087, 12 pages.
Lou et al., "Biodegradation of Polyethylene and Polystyrene by Greater Wax Moth Larvae (Galleria mellonella L.) and the Effect of Co-diet Supplementation on the Core Gut Microbiome", Database accession No. E20201208310881; & Environmental Science and Technology 20200303 American Chemical Society USA, Mar. 3, 2020, 54(5): 2821-2831.
Murugan et al., "A new biological recovery approach for PHA using mealworm, Tenebrio molitor", Journal of Biotechonology, 2016, 239: 98-105.

* cited by examiner

*Primary Examiner* — Yih-Horng Shiao
(74) *Attorney, Agent, or Firm* — James S. Keddie; Bozicevic, Field & Francis LLP

(57) ABSTRACT

The present disclosure relates to the production of biomass from at least one plastic polymer. More specifically, the present disclosure relates to use of a feed for production of biomass, wherein larvae of the family Pyralidae or of the family Tenebrionidae are fed on a feed comprising at least one plastic polymer, a related use of increasing pupation in a population of larva.

8 Claims, 6 Drawing Sheets

BIOMASS PRODUCTION

CROSS-REFERENCE TO RELATED APPLICATIONS

This application is a § 371 national phase of International Application No. PCT/EP2022/068350, filed on Jul. 1, 2022, which claims the benefit of European Application No. 21183517.8, filed on Jul. 2, 2021, European Application No. 21183520.2, filed on Jul. 2, 2021, and European Application No. 21210560.5, filed on Nov. 25, 2021, all of which applications are incorporated by reference herein.

TECHNICAL FIELD

The inventive concept described herein generally relates to production of biomass from at least one plastic polymer by utilization of insect larvae. More specifically, the present inventive concept relates to a method of production of biomass, a method of increasing pupation in a population of larva, and use of at least one plastic polymer for the production of biomass.

BACKGROUND

Plastics are synthetic polymers derived from fossil oil or renewable materials and largely resistant to biodegradation. Because of this resistance, plastics have a heavy environmental impact. Plastic pollution is such a serious problem, and worsening at rapid rate. Estimates state that by 2050 the world's oceans will contain more plastic than fish. Solutions to the problem of the plastic degradation and/or recycling are thus urgently needed. However, hundreds of different plastics exist and different plastics require different treatment for degradation and/or recycling. Plastic products often contain more than one part comprising different plastic polymers, making it difficult to separate the different plastics for degradation and/or recycling and many products comprise mixes of plastic polymers and/or copolymers. Additionally, the mixed way in which plastics are collected makes recycling very challenging, as the various types are difficult to separate. Thus, a large quantity of plastic materials is neither degraded or recycled and thus ends up polluting the environment.

The use of biomass for the production of energy as well as the production of food, feed and fertilizers, has attracted and continues to attract attention and interest in the current global environmental situation. The growing desire of industries to move away from fossil fuels and into renewable energy has increased the priority given to the production of biomass from organic matter derived from vegetable organisms, animals, bacteria and fungi, amongst others.

*Galleria mellonella*, with the common name greater wax moth, is a member of the family Pyralidae, which is a pest of the honeybee. It feeds on beeswax in the wild, i.e., mainly on esters formed by esterification of fatty acids with fatty alcohols. The skilled person appreciates an approximate chemical formula for beeswax being $C_{15}H_{31}COOC_{30}H_{61}$. The main constituents of beeswax are palmitate, palmitoleate, and oleate esters of long-chain (30-32 carbons) aliphatic alcohols. The principal consituents are triacontanyl palmitate $CH_3(CH_2)_{29}O—CO—(CH_2)_{14}CH_3$ and cerotic acid $CH_3(CH_2)_{24}COOH$, present in a ratio of approximately 6:1.

While being considered as a pest in the wild, it has been more appreciated in laboratory environments. *G. mellonella* is well-accepted as an insect model for studies relating to pathogen-host interactions and studies relating to antimicrobial compounds. The insect provides several advantages such low cost of maintenance, fast life cycle, the possibility of using a large number of larvae and an innate immune system which evolutionarily conserved relative to mammals.

WO 2014/067081 discloses insects capable of degrading petroleum-based plastics. The insects can be snout moths and the petroleum-based plastic can be amongst other polypropylene, polyurethane, polyamide or the polyacrylate polymethylmethacrylate.

In 2017, one group of researchers (Bombelli et al.) discovered that *G. mellonella* was able to consume polyethylene (PE) by the observance of holes in a plastic bag containing larvae. In 2020, another group of scientists (Lou et al.) have shown that *G. mellonella* is able to digest polystyrene (PS). This article teaches that larvae survival decreased when *G. mellonella* was feed polystyrene or polyethylene, compared to when *G. mellonella* was feed on beeswax or starved. Supplementing the plastic feed with *G. mellonellas* beeswax or bran, the survival rate of the larvae increased compared to when the feed was only polystyrene or polyethylene. As such, the study reports that *G. mellonella* exhibits a preference away from feeding on plastics.

Although effort has been made in the field of biomass production, there is a need for more methods for obtaining biomass. Would improved methods be provided, an even greater benefit for mankind would arise if such generation would be a result of degradation of unwanted waste materials.

DISCLOSURE OF THE INVENTION

It is an object of the present invention to at least partly reduce or overcome challenges in the prior art, and provide means for production of biomass via degradation of materials comprising at least one plastic polymer. The present inventors have surprisingly found that the production of biomass by digestion of various plastics only (without other feed supplement) can be achieved by the insects of the family Pyralidae while also increasing the pupation of said insects, whereby the survival and propagation of the biomass producing insects is improved and plastics are efficiently transformed to biomass. The present inventor also considers that insects of the order the Coleoptera may be utilized for production of biomass according to the present invention. In particular, the larvae of the family Tenebrionidae, in particular larvae of the species *Tenebrio molitor* and/or *Alphitobius diaperinus* are considered useful in this context. These and other objects are achieved in full, or at least in part, by aspects by the inventive concepts as disclosed herein.

In the first aspect, there is provided a method for producing biomass. Similarly, as discussed below in a fourth aspect there is provided a use of a feed for producing biomass. The method or a use comprises the steps of bringing at least one larva of the family Pyralidae or the family Tenebrionidae into contact with a feed and allowing said at least one larva to feed on said polymer. Thereby biomass is produced. The feed comprises at least one plastic polymer, which polymer is selected from the group consisting of polyethylene terephthalate, polypropylene, polyurethane, polyester, polyacrylate, polyglycol, polyvinyl chloride, polycarbonate, polyvinylidene chloride, synthetic polyamide, polypropylene terephthalate and polyether, poly(ethylene-vinylacetate), polyacrylonitrile, and any mixes or copolymers thereof or from the group consisting of polyethylene terephthalate, chloride, polycarbonate, polyvinylidene chloride, synthetic polyamide, polypropylene terephthalate and polyether, and any mixes or copolymers thereof.

Thus, there is provided a method for producing biomass, the method comprising bringing at least one larva of the family Pyralidae into contact with a feed, wherein said feed comprises at least one plastic polymer, wherein said polymer is selected from the group consisting of polyethylene terephthalate, polypropylene, polyurethane, polyester, polyacrylate, polyglycol, polyvinyl chloride, polycarbonate, polyvinylidene chloride, synthetic polyamide, polypropylene terephthalate and polyether, poly(ethylene-vinylacetate), polyacrylonitrile, and any mixes or copolymers thereof; or the group consisting of polyethylene terephthalate, polypropylene, polyurethane, polyester, polyacrylate, polyglycol, polyvinyl chloride, polycarbonate, polyvinylidene chloride, synthetic polyamide, polypropylene terephthalate and polyether, and any mixes or copolymers thereof, allowing said at least one larva to feed on said at least one plastic polymer, thereby producing biomass.

In one embodiment said polymer is selected from the group consisting of polyethylene terephthalate, polypropylene, polyurethane, polyester, polyacrylate, polyglycol, polyvinyl chloride, polycarbonate, polyvinylidene chloride, synthetic polyamide, polypropylene terephthalate and polyether, poly(ethylene-vinylacetate), polyacrylonitrile. In one embodiment said polymer is selected from the group consisting of polyethylene terephthalate, polyurethane, polyester, polyacrylate, polyglycol, polyvinyl chloride, polycarbonate, polyvinylidene chloride, synthetic polyamide, polypropylene terephthalate and polyether, poly(ethylene-vinylacetate), polyacrylonitrile. In one embodiment said polymer is selected from the group consisting of synthetic polyamide; polyacrylate; a mixture of synthetic polyamide and a copolymer of polyether-polyurethane; polyester; cotton; a mixture of polyester, synthetic polyamide and copolymer of polyether-polyurethane; and poly(ethylene-vinylacetate). In one embodiment said polymer is selected from the group consisting of synthetic polyamide; a mixture of synthetic polyamide and a copolymer of polyether-polyurethane; polyester; and poly(ethylene-vinylacetate). In one embodiment said polymer is selected from the group consisting of synthetic polyamide; polyester; and poly(ethylene-vinylacetate).

Thus according to a fourth aspect, there is also provided a use of a feed for producing biomass, the use comprising bringing at least one larva of the family Pyralidae into contact with said feed, wherein said feed comprises at least one plastic polymer, wherein said polymer is selected from the group consisting of polyethylene terephthalate, polypropylene, polyurethane, polyester, polyacrylate, polyglycol, polyvinyl chloride, polycarbonate, polyvinylidene chloride, synthetic polyamide, polypropylene terephthalate and polyether, poly(ethylene-vinylacetate), polyacrylonitrile, and any mixes or copolymers thereof; or the group consisting of polyethylene terephthalate, polypropylene, polyurethane, polyester, polyacrylate, polyglycol, polyvinyl chloride, polycarbonate, polyvinylidene chloride, synthetic polyamide, polypropylene terephthalate and polyether, and any mixes or copolymers thereof, allowing said at least one larva to feed on said at least one plastic polymer, thereby producing biomass.

For the avoidance of any doubt, all embodiments of said method according to the first aspect described herein are also applicable to said use of a feed according to the fourth aspect as disclosed herein, as apparent to a person of skill in the art.

An advantage of using a polymer from the lists of plastic polymers stated above is that the weight of the larvae is significantly increased compared to larvae feeding on natural feed. The term "natural feed" is intended to mean a feed of choice by the larvae when said larvae is in its natural environment. For example, natural feed may be wax-based feed for larva of the family Pyralidae and cereals, wheat, wheat bran etc. for larva of the family Tenebrionidae. For example, G. mellonella may feed on a wax-based feed, such as bees wax, i.e. mainly on esters formed by esterification of fatty acids with fatty alcohols. G. mellonella may additionally or alternatively feed on cast skins of bee larvae, pollen, propolis and honey. The skilled person is aware of what natural feed said larvae utilize in the natural environment.

Another advantage is that the weight increase is the result of plastic polymer degradation by the larvae. As such, degradation of unwanted material (plastic polymer) provides for biomass production. This is further described in the appended examples.

The present inventor have surprisingly found that when larva are fed plastic polymer based feed, the biomass (such as biomass in the form a larvae, pupae or feces) produced is significantly increased compared to biomass produced when said larva are fed their natural wax-based food, such as beeswax. As demonstrated in the Example section of the present application, the change of food source to a food source comprising at least one plastic polymer leads to an increase of larval mass over time compared to the natural wax-based food source. It is considered that the present invention provides a method or a use for the production of biomass, which simultaneously addresses the problem of the increasing amount of plastic waste in the environment.

Surprisingly, the mass increase of larvae that are fed exclusively on plastic (e.i. said material consist of plastic(s)) is achieved without supplementing said plastic with any supplementary feed (also referred to herein as additional feed). A supplementary feed is intended to mean a suitable natural feed for said larvae. Thus, advantageously, the production of biomass is achieved by said larvae without any requirement of addition of any supplement, such as feed supplement.

As said larvae are able to digest the herein disclosed plastic polymers, polymer mixes and copolymers, even without supplementing said plastic comprising material with any supplementary feed, the present invention provides advantages for plastic material degradation and recycling. Such advantage is for example that there is no need for the separation of different kinds of plastic materials when polymer mixes and/or copolymers. Another advantage is for example that there is no need to mix plastic materials subjected to degradation with a natural feed for said larvae, in order to achieve plastic digestion by said larvae. Furthermore, there is no need to mix plastic materials subjected to degradation with supplementary feed (which may be a natural feed for the species) for obtaining increased larval mass.

As used herein, the term "plastic" is intended to comprise both thermoset and thermoplastic materials as well as synthetic elastomers.

In one embodiment of said first or fourth aspect, the feed consists of said at least one plastic polymer, wherein said polymer is selected from the group consisting of polyethylene terephthalate, polypropylene, polyurethane, polyester, polyacrylate, polyglycol, polyvinyl chloride, polycarbonate, polyvinylidene chloride, synthetic polyamide, and any mixes or copolymers thereof. For avoidance of any doubt, when the feed consists of said at least one plastic polymer, there can be no supplementary feed added to the feed. Thus, said larvae feed only on plastic polymer(s). This is in line with the appended examples, wherein the feed is at least one plastic polymer, there is no supplementary feed available for the larvae.

A large number of plastic polymers is used by mankind often contain mixtures of polymers and/or copolymers, such as exemplified but not limited to the ones listed in the following embodiments. Thus, in one embodiment, the polymer is selected from the group consisting of polyethylene, polypropylene, polyurethane, synthetic polyamide, polyester, polyacrylate, polyether and any mixes or copolymers thereof.

In one embodiment, the polymer is selected from the group consisting of polypropylene, polyurethane, synthetic polyamide, polyester, and any mixes or copolymers thereof.

In one embodiment, the polymer is selected from the group consisting of polypropylene, polyurethane, synthetic polyamide and polyacrylate, and any mixes or copolymers thereof.

In one embodiment, the polymer is a mixture of synthetic polyamide and a polyether-polyurethane copolymer.

In one embodiment, the polymer is selected from the group consisting of polypropylene, polyurethane, and polyacrylate, and any mixes or copolymers thereof.

In the packaging industry, it is common to use different plastic polymers for different part of a package. Packaging materials often contain mixtures of polymers and/or copolymers, such as exemplified but not limited to the ones listed in the following embodiment. In one embodiment, the polymer is selected from the group consisting of polypropylene, polyethylene and polyethylene terephthalate, and any mixes or copolymers thereof.

A large number of plastic polymers are used in the clothing industry and clothing materials often contain mixtures of polymers and/or copolymers, such as exemplified but not limited to the ones listed in the following embodiment. Thus, in one embodiment, the polymer is selected from the group consisting of polypropylene, synthetic polyamide, polyacrylate, and polyester and any mixes or copolymers thereof.

In the transportation industry, there is a high demand on materials that can resist external forces. The materials often contain mixtures of polymers and/or copolymers, such as exemplified but not limited to the ones listed in the following embodiment. Thus, in one embodiment, the polymer is selected from the group consisting of polypropylene and polyurethane, and any mixes or copolymers thereof.

In the building and construction industry, there is a high demand on long-lasting materials or materials that can resist external forces and materials with good insulation properties. The materials often contain mixtures of polymers and/or copolymers, such as exemplified but not limited to the ones listed in the following embodiment. Thus, in one embodiment, the polymer is selected from the group consisting of polyacrylate, polypropylene and polyurethane, and any mixes or copolymers thereof.

A plastic material may often comprise more than one polymer. Commonly, a plastic material comprises mixes of polymers, or plastic copolymers. This is a problem for the waste industry because different plastics require different conditions and methods of treatment for degradation and/or recycling. As plastic products often contain many different plastic polymers (in the same or in different parts of the product) it is very challenging to sufficiently separate different plastics for efficient degradation and/or recycling. Additionally, the mixed way in which plastics are collected makes the recycling process very challenging due to mixed materials. This may lead to problems in degradation or recycling of the materials. Advantageously, the present disclosure provides a method or a use for degradation of a range of plastic-comprising materials. Many plastic materials consist of more than one type plastic polymer, either as a mixture, composite material or copolymer. Thus, it is considered advantageous that such plastic material may be fully digested. For example, it is envisioned that complete clothing items, whole or processed into fragments could be digested without the need to separate different polymers from each other. The method or use as disclosed herein may provide for effective degradation of many different plastic materials, as well as any mixes and/or copolymers thereof, while producing biomass.

In one embodiment, the at least one polymer is a mixture of at least two polymers. In one embodiment, the mixture of a least two different polymers, which polymers are independently selected from the group consisting of polyethylene terephthalate, polyethylene, polypropylene, polyurethane, polyester, polyacrylate, polystyrene, polyether, polyglycol, polyvinyl chloride, polycarbonate, and polyvinylidene chloride. In a related embodiment, the mixture of a least two polymers, which polymers are independently selected from the group consisting of polyethylene, polypropylene, and polyurethane. Optionally, the material may further comprise a polymer selected from the group consisting of synthetic polyamide and polyester, or any copolymers thereof.

In one embodiment, the at least one polymer is a mixture of at least two polymers. In one embodiment, the mixture of a least two different polymers, which polymers are independently selected from the group consisting of polyethylene terephthalate, polyethylene, polypropylene, polyurethane, polyester, polyacrylate, polyether, polyglycol, polyvinyl chloride, polycarbonate, and polyvinylidene chloride. In a related embodiment, the mixture of a least two polymers, which polymers are independently selected from the group consisting of polyethylene, polypropylene, and polyurethane. Optionally, the material may further comprise a polymer selected from the group consisting of synthetic polyamide and polyester, or any copolymers thereof.

In one embodiment, the polymer is a copolymer, which copolymer comprises at least two polymers, independently selected from the group consisting of polyethylene terephthalate, polyethylene, polypropylene, polyurethane, polyester, polyacrylate, polystyrene, polyether, polyglycol, polyvinyl chloride, polycarbonate, and polyvinylidene chloride, such as the group consisting of polyethylene terephthalate, polyethylene.

In one embodiment, the polymer is a copolymer, which copolymer comprises at least two polymers, independently selected from the group consisting of polyethylene terephthalate, polyethylene, polypropylene, polyurethane, polyester, polyacrylate, polyether, polyglycol, polyvinyl chloride, polycarbonate, and polyvinylidene chloride.

In one embodiment, the copolymer comprises at least two polymers, independently selected from the group consisting of polyether, polypropylene, and polyurethane, and optionally wherein said copolymer further comprises a polymer selected from the group consisting of synthetic polyamide and polyester, or any mixes thereof.

In one embodiment, the copolymer is a polyether-polyurethane copolymer, such as elastane.

In one embodiment, the copolymer further comprising an additional polymer.

In one embodiment, the copolymer further comprises a polymer selected from the group consisting of polyethylene, synthetic polyamide and a polysaccharide such as cellulose, or any mixes thereof.

In one embodiment, the copolymer further comprises a polymer selected from the group consisting of synthetic polyamide, polyester, polyacrylate, polyethylene and cellulose.

In one embodiment, the polyester is selected from the group consisting of polyethylene terephthalate, polypropylene terephthalate, polycaprolactone, and polyethylene adipate.

As used herein, the term "synthetic polyamide" refers to a polyamid which is made up of repeating units of the same kind. As such, a synthetic polyamide is different from for example a protein, which consists of different units and is obtained in a step-by-step type polymerization. A synthetic polymer, such as synthetic polyamide, may for example be obtained by step-growth polymerization. Examples of synthetic polyamides are for example nylons. In one embodiment, the synthetic polyamide is selected from the group consisting of PA 6; PA 6,6; PA 10 and PA 12.

In one particular embodiment of the method according to the first aspect or use according to the fourth aspect, wherein said at least one larva is of the family Pyralidae, the method or use exhibits an increase in pupation in a population of said larva compared to when a corresponding population of larva is fed a wax-based feed. This is evident from FIGS. 1-3. FIG. 1 shows that a larger amount of larvae of G. mellonella successfully transform into pupae when feed on the plastic material polypropylene than when feed on wax, which is a natural feed of G. mellonella. FIGS. 2-3 shows the difference in the amount of larvae of G. mellonella successfully transform into pupae when feed on a plastic polymer according to the invention, compared to when the feed is wax.

In one embodiment, said wax-based feed comprises esters formed by esterification of fatty acids with fatty alcohols. In one embodiment, said wax-based feed essentially consists of esters formed by esterification of fatty acids with fatty alcohols. In one embodiment, said wax-based feed is bees wax. In particular, said wax-based feed may comprise approximately at maximum 10%, such as approximately at maximum 5%, such as approximately at maximum 3%, such as approximately at maximum 1% by weight of a polymer selected from the group consisting of polyethylene, polyethylene terephthalate, polypropylene, polyurethane, polyamide, polyester, polyacrylate, polystyrene, polyether, polyglycol, polysaccharide, cellulose, polyvinyl chloride, polycarbonate, polyvinylidene chloride, and any mixes or copolymers thereof.

In one embodiment, the increase of pupation is quantified as the difference between the number of pupae versus dead larvae compared to the initial number of larvae in the population. Thus, the number of pupae versus dead larvae is compared in the population receiving the feed comprising or consisting of at least one plastic polymer with the corresponding population receiving the wax-based feed.

In another embodiment of the method according to the first aspect or use according to the fourth aspect, wherein said at least one larva is of the family Tenebrionidae, the method or use exhibits an increase in pupation in a population of said larva compared to when a corresponding population of larva is fed their natural feed, such as cereals, wheat or wheat bran. The skilled person appreciates that the number of pupae versus dead larvae may be compared in the population receiving the feed comprising or consisting of at least one plastic polymer with the corresponding population receiving said natural feed and quantified in the same manner as described above, in other words the increase of pupation may be quantified as the difference between the number of pupae versus dead larvae compared to the initial number of larvae in the population. In a related embodiment, at least one larva is of the family Tenebrionidae is *Tenebrio molitor* and/or *Alphitobius diaperinus*.

In one embodiment, said increase of pupation is after at least 4 days, such as at least 5 days, such as at least 6 days, such as at least 7 days, such as at least 8 days, such as at least 9 days, such as at least 10 days, such as at least 11 days, such as at least 12 days, such as at least 13 days, such as at least 14 days, such as at least 15 days, such as at least 16 days, such as at least 17 days, such as at least 18 days, such as at least 19 days, such as at least 20 days, such as at least 21 days, such as at least 22 days, such as at least 23 days, such as at least 24 days, such as at least 25 days, such as at least 26 days, such as at least 27 days, such as at least 28 days, such as at least 29 days, such as at least 30 days, such as at least 35 days, such as at least 40 days. In particular, said increase of pupation is approximately at least 5%, such as approximately at least 7%, such as approximately at least 10%, such as approximately at least 15%, such as approximately at least 20%, such as approximately at least 25%, such as approximately at least 30%, such as approximately at least 40%, such as approximately at least 50%, such as approximately at least 60%, such as approximately at least 70%, such as approximately at least 80%, such as approximately at least 90%, such as approximately at least 100%. Referring to Table 1, the % increase in pupation is remarkable for the tested substrates. For polyamide, the % increase at day 19 is 90%. For polyester, the % increase at day 19 is 97.5%. For polyacrylate, the % increase at day 19 is 52.5%. For cotton, the % increase at day 19 is 80%. For polyethylene, the % increase at day 19 is 57%. For a mixture of polyamide and a polyether-polyurethane copolymer, the % increase at day 19 is 87.5%. For a mixture of polyester, polyamide and a polyether-polyurethane copolymer, the % increase at day 19 is 60%. In one embodiment, said increase of pupation is within the range of from approximately 5 to approximately 50%, such as within the range of from approximately 10 to approximately 35%, such as within the range of from approximately 15 to approximately 25%, such as within the range of from approximately 18 to approximately 22%, such as around approximately 20%. In one embodiment, said increase of pupation is within the range of from approximately 15 to approximately at least 100%, such as within the range of from approximately 20 to approximately at least 100%, such as within the range of from approximately 40 to approximately at least 100%, such as within the range of from approximately 50 to approximately at least 100% such as within the range of from approximately 60 to approximately at least 100%, such as within the range of from approximately 70 to approximately at least 100%, such as within the range of from approximately 80 to approximately at least at least 100%, such as within the range of from approximately 90 to approximately at least 100%. In particular, said increase of pupation may be after at least 10 days, such as at least 14 days, such as at least 15 days or longer such as at least 19 days or longer, such as approximately 24 days. In particular if the larvae are kept under conditions as described herein, such as the conditions as described in Example 2.

In a second related aspect of the present disclosure, there is provided a method for increasing pupation in a population of larva of the family Pyralidae or the family Tenebrionidae. The method comprises bringing the population into contact with feed, wherein said feed comprises at least one polymer. The population is hereby allowed to feed on said feed. The polymer is selected from the group consisting of polyethylene, polyethylene terephthalate, polypropylene, polyurethane, polyamide, polyester, polyacrylate, polystyrene, polyether, polyglycol, polysaccharide, polyvinyl chloride, polycarbonate, polyvinylidene chloride, and any mixes or copolymers thereof. Alternatively, the polymer is selected from the group consisting of polyethylene, polyethylene terephthalate, polypropylene, polyurethane, polyamide, polyester, polyacrylate, polystyrene, polyether, polyglycol, polyvinyl chloride, polycarbonate, polyvinylidene chloride, and any mixes or copolymers thereof. In one embodiment, said polymer is selected from the group consisting of polyethylene, polyethylene terephthalate, polypropylene, polyurethane, polyester, polyacrylate, polyglycol, polyvinyl chloride, polycarbonate, polyvinylidene chloride, synthetic polyamide, polypropylene terephthalate and polyether, poly(ethylene-vinylacetate), polyacrylonitrile, and any mixes or copolymers thereof. In one embodiment, said polymer is selected from the group consisting of polyethylene, polyethylene terephthalate, polypropylene, polyurethane, polyamide, polyester, polyacrylate, polystyrene, polyether, polyglycol, polysaccharide, polyvinyl chloride, polycarbonate, polyvinylidene chloride, and any mixes or copolymers thereof. In one embodiment, said polymer is selected from the group consisting of polyethylene terephthalate, polypropylene, polyurethane, polyester, polyacrylate, polyglycol, polyvinyl chloride, polycarbonate, polyvinylidene chloride, synthetic polyamide, polypropylene terephthalate and polyether. In one embodiment, said polymer is selected from the group consisting of synthetic polyamide; polyacrylate; a mixture of synthetic polyamide and a copolymer of polyether-polyurethane; polyethylene; polyester; cotton; a mixture of polyester, synthetic polyamide and copolymer of polyether-polyurethane; polyethylene; and poly(ethylene-vinylacetate). In one embodiment, said polymer is selected from the group consisting of synthetic polyamide; a mixture of synthetic polyamide and a copolymer of polyether-polyurethane; polyethylene; polyester; and poly(ethylene-vinylacetate). In one embodiment, said polymer is selected from the group consisting of synthetic polyamide; polyester; and poly(ethylene-vinylacetate). The pupation is increased compared to when said feed is a wax-based feed for the family Pyralidae. The skilled person will appreciate that the comparison may be made in the same population of larvae at a different time or in a corresponding population as the same or a different time. In the case wherein the larvae of the family Pyralidae is *G. mellonella*, the natural feed may be a wax-based feed. Said wax-based feed may be bees wax, when said larvae are in their natural wildlife environment.

Thus, in the fifth aspect (related to said second aspect) there is also provided a use of a feed for increasing pupation in a population of larva of the family Pyralidae or the family Tenebrionidae. The use comprises bringing the population into contact said feed, wherein said feed comprises at least one polymer. The population is hereby allowed to feed on said feed. The polymer is selected from the group consisting of polyethylene, polyethylene terephthalate, polypropylene, polyurethane, polyamide, polyester, polyacrylate, polystyrene, polyether, polyglycol, polysaccharide, polyvinyl chloride, polycarbonate, polyvinylidene chloride, and any mixes or copolymers thereof. Alternatively, the polymer is selected from the group consisting of polyethylene, polyethylene terephthalate, polypropylene, polyurethane, polyamide, polyester, polyacrylate, polystyrene, polyether, polyglycol-polyvinyl chloride, polycarbonate, polyvinylidene chloride, and any mixes or copolymers thereof. Alternatively, the polymer is selected from the group consisting of polyethylene, polyethylene terephthalate, polypropylene, polyurethane, polyamide, polyester, polyacrylate, polystyrene, polyether, polyglycol, polyvinyl chloride, polycarbonate, polyvinylidene chloride, and any mixes or copolymers thereof. In one embodiment, said polymer is selected from the group consisting of polyethylene, polyethylene terephthalate, polypropylene, polyurethane, polyester, polyacrylate, polyglycol, polyvinyl chloride, polycarbonate, polyvinylidene chloride, synthetic polyamide, polypropylene terephthalate and polyether, poly(ethylene-vinylacetate), polyacrylonitrile, and any mixes or copolymers thereof. In one embodiment, said polymer is selected from the group consisting of polyethylene, polyethylene terephthalate, polypropylene, polyurethane, polyamide, polyester, polyacrylate, polystyrene, polyether, polyglycol, polysaccharide, polyvinyl chloride, polycarbonate, polyvinylidene chloride, and any mixes or copolymers thereof. In one embodiment, said polymer is selected from the group consisting of polyethylene terephthalate, polypropylene, polyurethane, polyester, polyacrylate, polyglycol, polyvinyl chloride, polycarbonate, polyvinylidene chloride, synthetic polyamide, polypropylene terephthalate and polyether. In one embodiment, said polymer is selected from the group consisting of synthetic polyamide; polyacrylate; a mixture of synthetic polyamide and a copolymer of polyether-polyurethane; polyethylene; polyester; cotton; a mixture of polyester, synthetic polyamide and copolymer of polyether-polyurethane; polyethylene; and poly(ethylene-vinylacetate). In one embodiment, said polymer is selected from the group consisting of synthetic polyamide; a mixture of synthetic polyamide and a copolymer of polyether-polyurethane; polyethylene; polyester; and poly(ethylene-vinylacetate). In one embodiment, said polymer is selected from the group consisting of synthetic polyamide; polyester; and poly(ethylene-vinylacetate). The pupation is increased compared to when said feed is a wax-based feed for the family Pyralidae. The skilled person will appreciate that the comparison may be made in the same population of larvae at a different time or in a corresponding population as the same or a different time. In the case wherein the larvae of the family Pyralidae is *G. mellonella*, the natural feed may be a wax-based feed. Said wax-based feed may be bees wax, when said larvae are in their natural wildlife environment.

All embodiments of said method described below are also applicable to the use of a feed, as apparent to a person of skill in the art.

Thus, in one embodiment of the second aspect as described herein, there is provided a method or use for increasing pupation in a population of larva of the family Pyralidae, the method or use comprising bringing said population into contact with feed and allowing the population to feed on said feed, wherein said feed comprises at least one polymer, wherein said polymer is selected from the group consisting of polyethylene, polyethylene terephthalate, polypropylene, polyurethane, polyamide, polyester, polyacrylate, polystyrene, polyether, polyglycol, polysaccharide, polyvinyl chloride, polycarbonate, polyvinylidene chloride, and any mixes or copolymers thereof, and wherein said pupation is increased compared to when a corresponding population is fed a wax-based feed.

Surprisingly, the present inventor has found that when a population of larva of the family Pyralidae is contacted with a feed comprises at least one polymer as outlined above; the pupation amount is increased in the population. This is in contrast to the prior art (Lou et al) which teaches decreased survival when larvae are feed polystyrene or polyethylene, with a slight increase in survival when wax-based feed is added to polystyrene or polyethylene diet.

In the case of a larva of the family Tenebrionidae, it is expected that the pupation is increased compared to when said larvae are fed their natural feed, such as cereals, wheat or wheat bran. The skilled person will appreciate that the embodiments of the second aspect as listed herein are also relevant for the embodiment of the method or use for increasing pupation in a population of larva of the family Tenebrionidae.

This effect is highly advantageous since it provides for generation of more biomass, and at the same time, degradation of more polymers, such as plastic polymers. According to the present disclosure, the feed may comprise at least 1 plastic polymer, such as at least 2 plastic polymers, such as at least 3 plastic polymers, such as at least 4 plastic polymers, such as at least 5 plastic polymers, such as at least 10 plastic polymers, such as at least 15 plastic polymers, such as at least 20 plastic polymers, such as at least 25 plastic polymers, such as at least 30 plastic polymers, such as at least 35 plastic polymers, such as at least 40 plastic polymers. In one embodiment, the feed consists of at least one plastic polymer, wherein said polymer is selected from the group consisting of polyethylene, polyethylene terephthalate, polypropylene, polyurethane, polyamide, polyester, polyacrylate, polystyrene, polyether, polyglycol, polysaccharide, polyvinyl chloride, polycarbonate, polyvinylidene chloride, and any mixes or copolymers thereof.

According to the present disclosure, the feed may consist of at least 1 plastic polymer, such as at least 2 plastic polymers, such as at least 3 plastic polymers, such as at least 4 plastic polymers, such as at least 5 plastic polymers, such as at least 10 plastic polymers, such as at least 15 plastic polymers, such as at least 20 plastic polymers, such as at least 25 plastic polymers, such as at least 30 plastic polymers, such as at least 35 plastic polymers, such as at least 40 plastic polymers.

According to the present disclosure, the feed may consist of at least 1 type of plastic polymer, such as at least 2 types of plastic polymers, such as at least 3 types of plastic polymers, such as at least 4 types of plastic polymers, such as at least 5 types of plastic polymers, such as at least 10 types of plastic polymers, such as at least 15 types of plastic polymers, such as at least 20 types of plastic polymers, such as at least 25 types of plastic polymers, such as at least 30 types of plastic polymers, such as at least 35 types of plastic polymers, such as at least 40 types of plastic polymers.

Due to the utility of a population of larva of the family Pyralidae and/or larva of the family Tenebrionidae and the results presented in the appended examples, the present inventor envisions that the feed may be a pure polymer, or a mixture of a few or many different polymers. As apparent to a person of skill in the art, the effect of increased pupation is plausible for both pure polymers, as well as any mixes or copolymers.

In one embodiment, the polymer is selected from the group consisting of polyethylene, polypropylene, polyurethane, polyamide, polyester, polyacrylate, polystyrene, cellulose and any mixes or copolymers thereof.

In one embodiment, the polymer is selected from the group consisting of polyethylene, polypropylene, polyurethane, polyamide, polyester, and any mixes or copolymers thereof.

In one embodiment, the said polymer is selected from the group consisting of polypropylene, polyurethane, polyamide and polyacrylate, and any mixes or copolymers thereof.

In one embodiment, the polymer is selected from the group consisting of polyester, polyamide, cellulose or a mixture of polyamide and a polyether-polyurethane copolymer In one embodiment, the polymer is selected from the group consisting of polypropylene, polyurethane, and polyacrylate, and any mixes or copolymers thereof.

In one embodiment, the polymer is selected from the group consisting of polypropylene, polyethylene, and polystyrene, and any mixes or copolymers thereof.

In one embodiment, the polymer is selected from the group consisting of polypropylene, polyamide, polyacrylate, polyester, and polyether, and any mixes or copolymers thereof.

In one embodiment, the polyether is a polysaccharide. Both synthetic and naturally derived polysaccharides are available, as appreciated by the skilled person. In one embodiment, said polysaccharide is a synthetic polysaccharide.

In one embodiment, said polysaccharide is a natural derived polysaccharide. In one embodiment, the polysaccharide is cellulose. In one embodiment, the cellulose is cotton.

In one embodiment, the polymer is selected from the group consisting of polypropylene, polyethylene, and polyurethane, and any mixes or copolymers thereof.

In one embodiment, the polymer is selected from the group consisting of polypropylene and polyurethane, and any mixes or copolymers thereof.

In one embodiment, the polymer is a synthetic polymer.

In one embodiment, the polyester is selected from the group consisting of polyethylene terephthalate, polypropylene terephthalate, polycaprolactone, and polyethylene adipate.

As discussed above for the first aspect, and as equally true for the second, the third, the fourth, or fifth aspect, a synthetic polyamide is made up of repeating units of the same kind. As such, is different from for example a protein, which consists of different unit and is obtained in a step-by-step type polymerization. A synthetic polymer may for example be obtained by step-growth polymerization. Examples of synthetic polyamides are for example nylons. The skilled person is aware of other types of synthetic polyamides. In one embodiment, the synthetic polyamide is selected from the group consisting of PA 6, PA 6,6, PA 10 and PA 12.

In one embodiment, the wax-based feed comprises approximately at maximum 10%, such as approximately at maximum 5%, such as approximately at maximum 3%, such as approximately at maximum 1% by weight of a polymer selected from the group consisting of polyethylene, polyethylene terephthalate, polypropylene, polyurethane, polyamide, polyester, polyacrylate, polystyrene, polyether, polyglycol, polysaccharide, cellulose, polyvinyl chloride, polycarbonate, polyvinylidene chloride, and any mixes or copolymers thereof. In one embodiment, the wax-based feed is beeswax. Beeswax is a natural product, and as such, may differ in exact composition. However, in one embodiment the beeswax mainly comprises palmitate, palmitoleate, and oleate esters of long-chain aliphatic alcohols.

In one embodiment, the increase of pupation is quantified as the difference between the number of pupae versus dead larvae compared to the initial number of larvae in said population. In this way, the increase of pupation is to be understood as that the number of larvae that form pupas is higher, and thus the survival of larvae that enter the next developmental stage is increased. Larvae that do not enter the developmental stage of pupation die instead.

Increased pupation may be observed already after four days in the population. In one embodiment, the increase of pupation is after at least 4 days, such as at least 5 days, such as at least 6 days, such as at least 7 days, such as at least 8 days, such as at least 9 days, such as at least 10 days, such as at least 11 days, such as at least 12 days, such as at least 13 days, such as at least 14 days, such as at least 15 days, such as at least 16 days, such as at least 17 days, such as at least 18 days, such as at least 19 days, such as at least 20 days, such as at least 21 days, such as at least 22 days, such as at least 23 days, such as at least 24 days, such as at least 25 days, such as at least 26 days, such as at least 27 days, such as at least 28 days, such as at least 29 days, such as at least 30 days, such as at least 35 days, such as at least 40 days.

In one embodiment, the increase of pupation is approximately at least 5%, such as approximately at least 7%, such as approximately at least 10%, such as approximately at least 15%, such as approximately at least 20%, such as approximately at least 25%, such as approximately at least 30%, such as approximately at least 40%, such as approximately at least 50%, such as approximately at least 60%, such as approximately at least 70%, such as approximately at least 80%, such as approximately at least 90%, such as approximately at least 100%.

In one embodiment, the increase of pupation is within the range of 5 to 50%, such as within the range of 10 to 35%, such as within the range of 15 to 25%, such as within the range of 18 to 22%, such as around 20%. In one embodiment, said increase of pupation is within the range of from approximately 20 to approximately 100%, such as within the range of from approximately 40 to approximately 100%, such as within the range of from approximately 50 to approximately 100%. In particular, said increase of pupation may be after at least 10 days, such as at least 14 days, such as at least 15 days or longer. In particular if the larvae are kept under conditions as described herein.

The biomass produced by the methods or uses disclosed herein is useful for many purposes, of which some are mentioned below. In one embodiment, the biomass comprises pupae of the family Pyralidae, and/or larvae of the family Pyralidae, and/or feces of said larvae, which may be extracted from the biomass. In one embodiment, the biomass comprises pupae of the family Pyralidae. Pupae may be used to maintain a population of larvae that can produce biomass by degradation of at least one plastic polymer. In one embodiment, the biomass comprises larvae of the family Pyralidae. The larvae may comprise nutrients in the form of lipids and/or proteins. In one embodiment, the biomass comprises feces of said larvae of the family Pyralidae. Feces of the larvae may serve useful as fertilizer. In one embodiment, the biomass further comprises polyethylene glycol.

In one embodiment, the biomass comprises pupae of the family Tenebrionidae, and/or larvae of the family Tenebrionidae, and/or feces of said larvae, which may be extracted from the biomass. In one embodiment, the biomass comprises pupae of the family Tenebrionidae. Pupae may be used to maintain a population of larvae that can produce biomass by degradation of at least one plastic polymer. In one embodiment, the biomass comprises larvae of the family Tenebrionidae. The larvae may comprise nutrients in the form of lipids and/or proteins. In one embodiment, the biomass comprises feces of said larvae of the family Tenebrionidae. Feces of the larvae may serve useful as fertilizer. In one embodiment, the biomass further comprises polyethylene glycol.

In one embodiment, the biomass is harvested after at least 5 days, such as 10 days, such as 15 days, such as 16 days, such as 17 days, such as 18 days, such as 19 days, such as 20 days, such as 21 days, such as 22 days, such as 23 days, such as 24 days, such as 25 days, such as 30 days, such as 35 days, such as 40 days, such as 45 days. As apparent for a person of skill in the art, the harvesting may be chosen so that harvester obtains as much as possible of his or hers preferred form of biomass.

In an embodiment of the method or use according any of the aspects as disclosed herein, there is provided a method or use of a feed for producing biomass, wherein the method or use is a continuous method or use. The method or use comprises the steps of:

a) providing a population of larvae B,
b) bringing said population into contact with a feed as defined in with the first or second aspect,
c) allowing an amount A of B to develop into pupae, and harvesting biomass comprising an amount (B-A) larvae,
d) allowing said pupae to transform into moths, and
e) allowing said moths to produce larvae, thereby obtaining a population of larvae B', and repeating steps a) to e).

It will be understood that that when the steps a) to e) are repeated, the B' population in step e) is used as the population B in step a). It is envisioned the steps a) to e) may be repeated hundreds or thousands of times, such as indefinitely.

To clarify, step b) of bringing the population into contact with a feed as defined in the first or second aspect is meant to be understood to encompass allowing the population of larvae to ingest said feed. Thus, step b) may be phrased as bringing said population into contact with a feed as defined in with the first or second aspect and allowing the population to feed on said feed.

In one embodiment, the method or use does not require external addition of larvae.

In one embodiment, the population of larvae B' is approximately ±1% of B, such as ±approximately 2% of B, such as ±approximately 3% of B, such as ±approximately 4% of B, such as ±approximately 5% of B, such as ±approximately 6% of B, such as ±approximately 7% of B, such as ±approximately 8% of B, such as ±approximately 9% of B, such as ±approximately 10% of B, such as ±approximately 11% of B, such as ±approximately 12% of B, such as ±approximately 13% of B, such as ±approximately 14% of B, such as ±approximately 15% of B, such as ±approximately 20% of B, such as ±approximately 25% of B.

In one embodiment, the amount A is approximately 0.5% of B, such as approximately 1% of B, such as approximately 2% of B, such as approximately 3% of B, such as approximately 4% of B, such as approximately 5% of B, such as approximately 6% of B, such as approximately 7% of B, such as approximately 8% of B, such as approximately 9% of B, such as approximately 10% of B, such as approximately 11% of B, such as approximately 12% of B, such as approximately 13% of B, such as approximately 14% of B, such as approximately 15% of B, such as approximately 16% of B, such as approximately 17% of B, such as approximately 18% of B, such as approximately 19% of B, such as approximately 20% of B, such as approximately 25% of B, such as approximately 30% of B, such as approximately 35% of B, such as approximately 40% of B, such as approximately 45% of B, such as approximately 50% of B.

Without been bound by theory, it is considered that the continuous method or use of a feed may be beneficial as it does not require addition of external larvae, instead the larvae that hatch within the system are sufficient to allow for the system to be continuously self contained. Such a method or use would require minimal operation and supervision except of the addition of feed as well as the harvesting of biomass. Within the system an amount A of the total larvae B, would be allowed to develop into pupae, transform to insects and lay eggs, which when hatch to larvae and make up the total amount B'. The B' amount is sufficient to repopulate the system as well as allow for the harvesting a subset thereof as biomass. Thus, each cycle of steps a)-e) would lead to a new opportunity for harvesting biomass.

The present inventor has found it plausible that the inventive concepts as disclosed herein extends to the use of related species for the production of biomass by plastic digestion. In another aspect of the present disclosure, the methods according to the first aspect, may rely of the use of an alternative larva, such as a larva of the family Crambidae, or a larva of the order of Coleoptera, such as the of the family Tenebrionidae. or a larva of the genus *Plodia*, such as a larva of the species *Plodia interpunctella*. It is reasonable to expect that this is fruitful due to members of Coleoptera have been shown to digest polystyrene and polyethylene, members of the genus *Plodia* have been shown to degrade polyethylene and the family Crambidae is closely related with Pyralidae.

In one embodiment, when the at least one larva is of the family Pyralidae, the at least one larva of the family Pyralidae is selected from the group consisting of *Aglossa pinguinalis, Cadra cautella, Dioryctria abietella, Crambus lathoniellus, Aphomia sociella, Ephestia elutella, Plodia interpunctella, Paralipsa gularis, Zophodia grossulariella, Ephestia kuehniella, Evergestis forficalis, Ostrinia nubilalis, Pyralis farinalis, Acentria ephemerella, Achroia grisella* and *Galleria mellonella*.

In one embodiment, when the at least one larva is of the family Pyralidae, the at least one larva of the family Pyralidae is a member of the genus *Galleria*. In one embodiment said member of the genus *Galleria* is selected from the group consisting of *Galleria austrina, Galleria cerea, Galleria cerealis, Galleria cereana, Galleria cerella, Galleria crombruggheela, Galleria obliquella, Galleria mellonella*.

In one embodiment, when the at least one larva is of the family Pyralidae, the at least one larva of the family Pyralidae is *Achroia grisella*.

In one specifically preferred embodiment, the at least one larva of the family Pyralidae is at least one larva of the species *Galleria mellonella*.

In one embodiment, when the at least one larva is of the family Tenebrionidae, is selected from the group consisting of *Tenebrio molitor* and *Alphitobius diaperinus*. In one embodiment, said at least one larva is of the species *Tenebrio molitor*. In one embodiment, said at least one larva is of the species *Alphitobius diaperinus*.

In one embodiment, the method or use of a feed according to any one of the aspects as disclosed herein, is performed in a closed system. A closed system means that the method is performed or use is in a room or a closed container or the like, from which any larvae or pupae or moths may not escape. Advantageously, in a closed system conditions such as light, temperature or humidity, may be kept constant, or may be changed upon users own preference. Thus said conditions are controlled which allows for control of the life cycles of the insects as well as of the biomass production process.

In one embodiment, the larvae are brought into contact with said feed in a container. The container may be made up of for example glass, metals, metal alloys, composites, or treated wood, and any mixes thereof.

In one particular embodiment, the method or use of a feed comprises placing the larva in the container at a density of 0.2-5 larvae per $cm^2$, such as 0.2-3 larvae per $cm^2$, such as 0.2-2 larvae per $cm^2$ or such as 0.5-3 larvae per $cm^2$, such as 0.5-2 larvae per $cm^2$, such as 1-2 larvae per $cm^2$. As apparent for a person of skill in the art, higher density may be preferable for industrial purposes in order to provide higher production of biomass per area unit. However, high density is often avoided as it can contribute to cannibalism of the larvae. In one embodiment, the larvae exhibit no significant cannibalism, such as no cannibalism at all or less than 5%, such as less than 3%, such as less than 2%, such as less than 1% cannibalism.

The larva of the family Pyralidae and/or Tenebrionidae may survive in a variety of conditions. For example, the life cycle of *G. mellonella* comprises a larval stage that transforms within 6-8 weeks into pupae and finally into moth. The larvae are fairly large in size, the last instar larva is 2 cm long and 250 mg, or even up to 400-500 mg, in weight and can survive at various temperatures, such as 4-40° C. The larvae prefer temperatures in the range of 20-30° C. It is considered that the maintaining conditions beneficial to growth and metamorphosis may be advantageous for production of biomass. In one embodiment, the method is performed or use of a feed is at a temperature of from 4° C. to 40° C., such as from 15° C. to 35° C., preferably of from 20° C. to 30° C., most preferably of from 25° C. to 27° C. In one embodiment, the method is performed or use is at a humidity of from 30% to 99%. In one preferred embodiment, the humidity is maintained at approximately 80.0+/−10%, such as at approximately 80.0+/−5%.

Without being bound by any theory, it is considered that starvation of larva prior to providing the larva will plastic polymer based feed may lead to more efficient consumption, and thus degradation, of plastic polymers as disclosed herein. In one embodiment, the larva is subjected to starvation prior to adding any feed. In one embodiment, the starvation is for 1 to 20 days, such as for 1 to 10, such as for 1 to 5 days, such as for 2 days.

In third aspect, there is provided use of at least one polymer for production of biomass. The biomass comprises at least one member of the family Pyralidae or of the family Tenebrionidae. The at least one polymer may be selected from the group consisting of polyethylene terephthalate, polypropylene, polyurethane, polyester, polyacrylate, polystyrene, polyglycol, polyvinyl chloride, polycarbonate, polyvinylidene chloride, and any mixes or copolymers thereof. Thus, there is provided a use of at least one plastic polymer for production of biomass, wherein said biomass comprises at least one member of the family Pyralidae or of the family Tenebrionidae and wherein said at least one polymer is selected from the group consisting of polyethylene terephthalate, polypropylene, polyurethane, polyester, polyacrylate, polystyrene, polyglycol, polyvinyl chloride, polycarbonate, polyvinylidene chloride, and any mixes or copolymers thereof. In this context, the polymer is digested by members of the family Pyralidae or of the family Tenebrionidae, leading to increase in mass of said members and allows for harvesting at least a subset of the members as biomass.

In one embodiment, wherein the at least one larvae is of the family Pyralidae, the at least one larva of the family Pyralidae is selected from the group consisting of *Aglossa pinguinalis*, *Cadra cautella*, *Dioryctria abietella*, *Crambus lathoniellus*, *Aphomia sociella*, *Ephestia elutella*, *Plodia interpunctella*, *Paralipsa gularis*, *Zophodia grossulariella*, *Ephestia kuehniella*, *Evergestis forficalis*, *Ostrinia nubilalis*, *Pyralis farinalis*, *Acentria ephemerella*, *Achroia grisella* and *Galleria mellonella*.

In one embodiment, when the at least one larvae is of the family Pyralidae, the at least one larva of the family Pyralidae is a member of the genus *Galleria*, which member is selected from the group consisting of *Galleria austrina*, *Galleria cerea*, *Galleria cerealis*, *Galleria cereana*, *Galleria cerella*, *Galleria crombruggheela*, *Galleria obliquella*, *Galleria mellonella*.

In one embodiment, when the at least one larva is of the family Pyralidae, the at least one larva of the family Pyralidae is *Achroia grisella*.

In one specifically preferred embodiment, the at least one larva of the family Pyralidae is at least one larva of the species *Galleria mellonella*.

In one embodiment, wherein the at least one larvae is of the family Tenebrionidae, the at least one larva is of the species *Tenebrio molitor* or *Alphitobius diaperinus*.

In one embodiment of the method or use of a feed according to any one of the aspects as disclosed herein or of the use according to third aspect as disclosed herein, said polymer may be selected from any one of the below listed groups. The skilled person will appreciate that said groups are equally relevant for the any of said aspects and are not repeated in connection of each of the aspects only for the sake of brevity.

Thus, in one embodiment of any one of aspects one, two or three as disclosed above, said polymer is selected from the group consisting of polypropylene. In one embodiment, said polymer is selected from the group consisting of polyurethane. In one embodiment, said polymer is selected from the group consisting of synthetic polyamide. In one embodiment, said polymer is selected from the group consisting of polyacrylate. In one embodiment, said polymer is selected from the group consisting of polyethylene terephthalate. In one embodiment, said polymer is selected from the group consisting of polyester. In one embodiment, said polymer is selected from the group consisting of polypropylene, and polyurethane. In one embodiment, said polymer is selected from the group consisting of polypropylene, and synthetic polyamide. In one embodiment, said polymer is selected from the group consisting of polypropylene, and polyacrylate. In one embodiment, said polymer is selected from the group consisting of polypropylene, and polyethylene terephthalate. In one embodiment, said polymer is selected from the group consisting of polypropylene, and polyester. In one embodiment, said polymer is selected from the group consisting of polyurethane, and synthetic polyamide. In one embodiment, said polymer is selected from the group consisting of polyurethane, and polyacrylate. In one embodiment, said polymer is selected from the group consisting of polyurethane, and polyethylene terephthalate. In one embodiment, said polymer is selected from the group consisting of polyurethane, and polyester. In one embodiment, said polymer is selected from the group consisting of synthetic polyamide, and polyacrylate. In one embodiment, said polymer is selected from the group consisting of synthetic polyamide, and polyethylene terephthalate. In one embodiment, said polymer is selected from the group consisting of synthetic polyamide, and polyester. In one embodiment, said polymer is selected from the group consisting of polyacrylate, and polyethylene terephthalate. In one embodiment, said polymer is selected from the group consisting of polyacrylate, and polyester. In one embodiment, said polymer is selected from the group consisting of polyethylene terephthalate, and polyester. In one embodiment, said polymer is selected from the group consisting of polypropylene, polyurethane, and synthetic polyamide. In one embodiment, said polymer is selected from the group consisting of polypropylene, polyurethane, and polyacrylate. In one embodiment, said polymer is selected from the group consisting of polypropylene, polyurethane, and polyethylene terephthalate. In one embodiment, said polymer is selected from the group consisting of polypropylene, polyurethane, and polyester. In one embodiment, said polymer is selected from the group consisting of polypropylene, synthetic polyamide, and polyacrylate. In one embodiment, said polymer is selected from the group consisting of polypropylene, synthetic polyamide, and polyethylene terephthalate. In one embodiment, said polymer is selected from the group consisting of polypropylene, synthetic polyamide, and polyester. In one embodiment, said polymer is selected from the group consisting of polypropylene, polyacrylate, and polyethylene terephthalate. In one embodiment, said polymer is selected from the group consisting of polypropylene, polyacrylate, and polyester. In one embodiment, said polymer is selected from the group consisting of polypropylene, polyethylene terephthalate, and polyester. In one embodiment, said polymer is selected from the group consisting of polyurethane, synthetic polyamide, and polyacrylate. In one embodiment, said polymer is selected from the group consisting of polyurethane, synthetic polyamide, and polyethylene terephthalate. In one embodiment, said polymer is selected from the group consisting of polyurethane, synthetic polyamide, and polyester. In one embodiment, said polymer is selected from the group consisting of polyurethane, polyacrylate, and polyethylene terephthalate. In one embodiment, said polymer is selected from the group consisting of polyurethane, polyacrylate, and polyester. In one embodiment, said polymer is selected from the group consisting of polyurethane, polyethylene terephthalate, and polyester. In one embodiment, said polymer is selected from the group consisting of synthetic polyamide, polyacrylate, and polyethylene terephthalate. In one embodiment, said polymer is selected from the group consisting of synthetic polyamide, polyacrylate, and polyester. In one embodiment, said polymer is selected from the group consisting of synthetic polyamide, polyethylene terephthalate, and polyester. In one embodiment, said polymer is selected from the group consisting of polyacrylate, polyethylene terephthalate, and polyester. In one embodiment, said polymer is selected from the group consisting of polypropylene, polyurethane, synthetic polyamide, and polyacrylate. In one embodiment, said polymer is selected from the group consisting of polypropylene, polyurethane, synthetic polyamide, and polyethylene terephthalate. In one embodiment, said polymer is selected from the group consisting of polypropylene, polyurethane, synthetic polyamide, and polyester. In one embodiment, said polymer is selected from the group consisting of polypropylene, polyurethane, polyacrylate, and polyethylene terephthalate. In one embodiment, said polymer is selected from the group consisting of polypropylene, polyurethane, polyacrylate, and polyester. In one embodiment, said polymer is selected from the group consisting of polypropylene, polyurethane, polyethylene terephthalate, and polyester. In one embodiment, said polymer is selected from the group consisting of polypropylene, synthetic polyamide, polyacrylate, and polyethylene terephthalate. In one embodiment, said polymer is selected from the group consisting of polypropylene, synthetic polyamide, polyacrylate, and polyester. In one embodiment, said polymer is selected from the group consisting of polypropylene, synthetic polyamide, polyethylene terephthalate, and polyester. In one embodiment, said polymer is selected from the group consisting of polypropylene, polyacrylate, polyethylene terephthalate, and polyester. In one embodiment, said polymer is selected from the group consisting of polyurethane, synthetic polyamide, polyacrylate, and polyethylene terephthalate. In one embodiment, said polymer is selected from the group consisting of polyurethane, synthetic polyamide, polyacrylate, and polyester. In one embodiment, said polymer is selected from the group consisting of polyurethane, synthetic polyamide, polyethylene terephthalate, and polyester. In one embodiment, said polymer is selected from the group consisting of polyurethane, polyacrylate, polyethylene terephthalate, and polyester. In one embodiment, said polymer is selected from the group consisting of synthetic polyamide, polyacrylate, polyethylene terephthalate, and polyester. In one embodiment, said polymer is selected from the group consisting of polypropylene, polyurethane, synthetic polyamide, polyacrylate, and polyethylene terephthalate. In one embodiment, said polymer is selected from the group consisting of polypropylene, polyurethane, synthetic polyamide, polyacrylate, and polyester. In one embodiment, said polymer is selected from the group consisting of polypropylene, polyurethane, synthetic polyamide, polyethylene terephthalate, and polyester. In one embodiment, said polymer is selected from the group consisting of polypropylene, polyurethane, polyacrylate, polyethylene terephthalate, and polyester. In one embodiment, said polymer is selected from the group consisting of polypropylene, synthetic polyamide, polyacrylate, polyethylene terephthalate, and polyester. In one embodiment, said polymer is selected from the group consisting of polyurethane, synthetic polyamide, polyacrylate, polyethylene terephthalate, and polyester. In one embodiment, said polymer is selected from the group consisting of polypropylene, polyurethane, synthetic polyamide, polyacrylate, polyethylene terephthalate, and polyester.

In one embodiment, said polymer is selected from the group consisting of polyvinyl chloride, polyacrylate, synthetic polyamide, polyurethane, polyester, and any mixes or copolymers thereof;
  such as the group consisting of polyvinyl chloride, polyacrylate, synthetic polyamide, polyurethane, and any mixes or copolymers thereof;
  such as the group consisting of polyvinyl chloride, polyacrylate, synthetic polyamide, and any mixes or copolymers thereof;
  such as the group consisting of polyvinyl chloride, polyacrylate, and any mixes or copolymers thereof;
  such as the group consisting of polyvinyl chloride, and any mixes or copolymers thereof.

In another embodiment, said polymer is selected from the group consisting of polyvinyl chloride, polyacrylate, synthetic polyamide, polyurethane, polyester, and any mixes or copolymers thereof, and copolymers of polyether-polyurethane, polyacrylonitrile and polyethylene, and any mixes thereof;
  such as the group consisting of polyvinyl chloride, polyacrylate, synthetic polyamide, polyurethane, and any mixes or copolymers thereof, and copolymers of polyether-polyurethane, polyacrylonitrile and polyethylene, and any mixes thereof;
  such as the group consisting of polyvinyl chloride, polyacrylate, synthetic polyamide, and any mixes or copolymers thereof, and copolymers of polyether-polyurethane, polyacrylonitrile and polyethylene, and any mixes thereof;
  such as the group consisting of polyvinyl chloride, polyacrylate, and any mixes or copolymers thereof, and copolymers of polyether-polyurethane, polyacrylonitrile and polyethylene, and any mixes thereof;
  such as the group consisting of polyvinyl chloride, and any mixes or copolymers thereof, and copolymers of polyether-polyurethane, polyacrylonitrile and polyethylene, and any mixes thereof.

In another embodiment, said polymer is selected from the group consisting of polyvinyl chloride, polyacrylate, synthetic polyamide, polyurethane, polyester, and any mixes or copolymers thereof, and copolymers of polyacrylonitrile and copolymers of polyethylene, and any mixes thereof;
  such as the group consisting of polyvinyl chloride, polyacrylate, synthetic polyamide, polyurethane, and any mixes or copolymers thereof, and copolymers of polyacrylonitrile and copolymers of polyethylene, and any mixes thereof;
  such as the group consisting of polyvinyl chloride, polyacrylate, synthetic polyamide, and any mixes or copolymers thereof, and copolymers of polyacrylonitrile and copolymers of polyethylene, and any mixes thereof;
  such as the group consisting of polyvinyl chloride, polyacrylate, and any mixes or copolymers thereof, and copolymers of polyacrylonitrile and copolymers of polyethylene, and any mixes thereof;
  such as the group consisting of polyvinyl chloride, and any mixes or copolymers thereof, and copolymers of polyacrylonitrile and copolymers of polyethylene, and any mixes thereof.

In another embodiment, said polymer is selected from the group consisting of polyvinyl chloride, polyacrylate, synthetic polyamide, polyurethane, polyester, and any mixes or copolymers thereof, and copolymers of polyacrylonitrile, and any mixes thereof;
  such as the group consisting of polyvinyl chloride, polyacrylate, synthetic polyamide, polyurethane, and any mixes or copolymers thereof, and copolymers of polyacrylonitrile, and any mixes thereof;
  such as the group consisting of polyvinyl chloride, polyacrylate, synthetic polyamide, and any mixes or copolymers thereof, and copolymers of polyacrylonitrile, and any mixes thereof;
  such as the group consisting of polyvinyl chloride, polyacrylate, and any mixes or copolymers thereof, and copolymers of polyacrylonitrile, and any mixes thereof;
  such as the group consisting of polyvinyl chloride, and any mixes or copolymers thereof, and copolymers of polyacrylonitrile, and any mixes thereof.

In another embodiment, said polymer is selected from the group consisting of polyvinyl chloride, polyacrylate, synthetic polyamide, polyurethane, polyester, and any mixes or copolymers thereof, and copolymers of polyacrylonitrile and copolymers of polyethylene;
  such as the group consisting of polyvinyl chloride, polyacrylate, synthetic polyamide, polyurethane, and any mixes or copolymers thereof, and copolymers of polyacrylonitrile and copolymers of polyethylene;
  such as the group consisting of polyvinyl chloride, polyacrylate, synthetic polyamide, and any mixes or copolymers thereof, and copolymers of polyacrylonitrile and copolymers of polyethylene;
such as the group consisting of polyvinyl chloride, polyacrylate, and any mixes or copolymers thereof, and copolymers of polyacrylonitrile and copolymers of polyethylene;
such as the group consisting of polyvinyl chloride, and any mixes or copolymers thereof, and copolymers of polyacrylonitrile and copolymers of polyethylene.

In another embodiment, said polymer is selected from the group consisting of polyvinyl chloride, polyacrylate, synthetic polyamide, polyurethane, polyester, and any mixes or copolymers thereof, and copolymers of polyacrylonitrile;
such as the group consisting of polyvinyl chloride, polyacrylate, synthetic polyamide, polyurethane, and any mixes or copolymers thereof, and copolymers of polyacrylonitrile;
such as the group consisting of polyvinyl chloride, polyacrylate, synthetic polyamide, and any mixes or copolymers thereof, and copolymers of polyacrylonitrile;
such as the group consisting of polyvinyl chloride, polyacrylate, and any mixes or copolymers thereof, and copolymers of polyacrylonitrile;
such as the group consisting of polyvinyl chloride, and any mixes or copolymers thereof, and copolymers of polyacrylonitrile.

In one embodiment, said polymer is selected from the group consisting of poly(ethylene-vinyl acetate). In one embodiment, said polymer is selected from the group consisting of poly(ethylene-vinyl acetate), and polyurethane. In one embodiment, said polymer is selected from the group consisting of poly(ethylene-vinyl acetate), and synthetic polyamide. In one embodiment, said polymer is selected from the group consisting of poly(ethylene-vinyl acetate), and polyacrylate. In one embodiment, said polymer is selected from the group consisting of poly(ethylene-vinyl acetate), and polyethylene terephthalate. In one embodiment, said polymer is selected from the group consisting of poly(ethylene-vinyl acetate), and polyester. In one embodiment, said polymer is selected from the group consisting of poly(ethylene-vinyl acetate), polyurethane, and synthetic polyamide. In one embodiment, said polymer is selected from the group consisting of poly(ethylene-vinyl acetate), polyurethane, and polyacrylate. In one embodiment, said polymer is selected from the group consisting of poly(ethylene-vinyl acetate), polyurethane, and polyethylene terephthalate. In one embodiment, said polymer is selected from the group consisting of poly(ethylene-vinyl acetate), polyurethane, and polyester. In one embodiment, said polymer is selected from the group consisting of poly(ethylene-vinyl acetate), synthetic polyamide, and polyacrylate. In one embodiment, said polymer is selected from the group consisting of poly(ethylene-vinyl acetate), synthetic polyamide, and polyethylene terephthalate. In one embodiment, said polymer is selected from the group consisting of poly(ethylene-vinyl acetate), synthetic polyamide, and polyester. In one embodiment, said polymer is selected from the group consisting of poly(ethylene-vinyl acetate), polyacrylate, and polyethylene terephthalate. In one embodiment, said polymer is selected from the group consisting of poly(ethylene-vinyl acetate), polyacrylate, and polyester. In one embodiment, said polymer is selected from the group consisting of poly(ethylene-vinyl acetate), polyethylene terephthalate, and polyester. In one embodiment, said polymer is selected from the group consisting of poly(ethylene-vinyl acetate), polyurethane, synthetic polyamide, and polyacrylate. In one embodiment, said polymer is selected from the group consisting of poly(ethylene-vinyl acetate), polyurethane, synthetic polyamide, and polyethylene terephthalate. In one embodiment, said polymer is selected from the group consisting of poly(ethylene-vinyl acetate), polyurethane, synthetic polyamide, and polyester. In one embodiment, said polymer is selected from the group consisting of poly(ethylene-vinyl acetate), polyurethane, polyacrylate, and polyethylene terephthalate. In one embodiment, said polymer is selected from the group consisting of poly(ethylene-vinyl acetate), polyurethane, polyacrylate, and polyester. In one embodiment, said polymer is selected from the group consisting of poly(ethylene-vinyl acetate), polyurethane, polyethylene terephthalate, and polyester. In one embodiment, said polymer is selected from the group consisting of poly(ethylene-vinyl acetate), synthetic polyamide, polyacrylate, and polyethylene terephthalate. In one embodiment, said polymer is selected from the group consisting of poly(ethylene-vinyl acetate), synthetic polyamide, polyacrylate, and polyester. In one embodiment, said polymer is selected from the group consisting of poly(ethylene-vinyl acetate), synthetic polyamide, polyethylene terephthalate, and polyester. In one embodiment, said polymer is selected from the group consisting of poly(ethylene-vinyl acetate), polyacrylate, polyethylene terephthalate, and polyester. In one embodiment, said polymer is selected from the group consisting of poly(ethylene-vinyl acetate), polyurethane, synthetic polyamide, polyacrylate, and polyethylene terephthalate. In one embodiment, said polymer is selected from the group consisting of poly(ethylene-vinyl acetate), polyurethane, synthetic polyamide, polyacrylate, and polyester. In one embodiment, said polymer is selected from the group consisting of poly(ethylene-vinyl acetate), polyurethane, synthetic polyamide, polyethylene terephthalate, and polyester. In one embodiment, said polymer is selected from the group consisting of poly(ethylene-vinyl acetate), polyurethane, polyacrylate, polyethylene terephthalate, and polyester. In one embodiment, said polymer is selected from the group consisting of poly(ethylene-vinyl acetate), synthetic polyamide, polyacrylate, polyethylene terephthalate, and polyester. In one embodiment, said polymer is selected from the group consisting of poly(ethylene-vinyl acetate), polyurethane, synthetic polyamide, polyacrylate, polyethylene terephthalate, and polyester.

In one embodiment, said polymer is selected from the group consisting of poly(acrylonitrile-butadiene) and poly(ethylene-vinyl acetate). In one embodiment, said polymer is selected from the group consisting of poly(acrylonitrile-butadiene) and polyurethane. In one embodiment, said polymer is selected from the group consisting of poly(acrylonitrile-butadiene) and synthetic polyamide. In one embodiment, said polymer is selected from the group consisting of poly(acrylonitrile-butadiene) and polyacrylate. In one embodiment, said polymer is selected from the group consisting of poly(acrylonitrile-butadiene) and polyethylene terephthalate. In one embodiment, said polymer is selected from the group consisting of poly(acrylonitrile-butadiene) and polyester. In one embodiment, said polymer is selected from the group consisting of poly(acrylonitrile-butadiene), poly(ethylene-vinyl acetate), and polyurethane. In one embodiment, said polymer is selected from the group consisting of poly(acrylonitrile-butadiene), poly(ethylene-vinyl acetate), and synthetic polyamide. In one embodiment, said polymer is selected from the group consisting of poly(acrylonitrile-butadiene), poly(ethylene-vinyl acetate), and polyacrylate. In one embodiment, said polymer is selected from the group consisting of poly(acrylonitrile-butadiene), poly(ethylene-vinyl acetate), and polyethylene terephthalate. In one embodiment, said polymer is selected from the group consisting of poly(acrylonitrile-butadiene), poly(ethylene-vinyl acetate), and polyester. In one embodiment, said polymer is selected from the group consisting of poly (acrylonitrile-butadiene), polyurethane, and synthetic polyamide. In one embodiment, said polymer is selected from the group consisting of poly(acrylonitrile-butadiene), polyurethane, and polyacrylate. In one embodiment, said polymer is selected from the group consisting of poly(acrylonitrile-butadiene), polyurethane, and polyethylene terephthalate. In one embodiment, said polymer is selected from the group consisting of poly(acrylonitrile-butadiene), polyurethane, and polyester. In one embodiment, said polymer is selected from the group consisting of poly(acrylonitrile-butadiene), synthetic polyamide, and polyacrylate. In one embodiment, said polymer is selected from the group consisting of poly(acrylonitrile-butadiene), synthetic polyamide, and polyethylene terephthalate. In one embodiment, said polymer is selected from the group consisting of poly(acrylonitrile-butadiene), synthetic polyamide, and polyester. In one embodiment, said polymer is selected from the group consisting of poly(acrylonitrile-butadiene), polyacrylate, and polyethylene terephthalate. In one embodiment, said polymer is selected from the group consisting of poly(acrylonitrile-butadiene), polyacrylate, and polyester. In one embodiment, said polymer is selected from the group consisting of poly(acrylonitrile-butadiene), polyethylene terephthalate, and polyester. In one embodiment, said polymer is selected from the group consisting of poly(acrylonitrile-butadiene), poly(ethylene-vinyl acetate), polyurethane, and synthetic polyamide. In one embodiment, said polymer is selected from the group consisting of poly(acrylonitrile-butadiene), poly(ethylene-vinyl acetate), polyurethane, and polyacrylate. In one embodiment, said polymer is selected from the group consisting of poly(acrylonitrile-butadiene), poly(ethylene-vinyl acetate), polyurethane, and polyethylene terephthalate. In one embodiment, said polymer is selected from the group consisting of poly(acrylonitrile-butadiene), poly(ethylene-vinyl acetate), polyurethane, and polyester. In one embodiment, said polymer is selected from the group consisting of poly(acrylonitrile-butadiene), poly(ethylene-vinyl acetate), synthetic polyamide, and polyacrylate. In one embodiment, said polymer is selected from the group consisting of poly(acrylonitrile-butadiene), poly(ethylene-vinyl acetate), synthetic polyamide, and polyethylene terephthalate. In one embodiment, said polymer is selected from the group consisting of poly(acrylonitrile-butadiene), poly(ethylene-vinyl acetate), synthetic polyamide, and polyester. In one embodiment, said polymer is selected from the group consisting of poly(acrylonitrile-butadiene), poly(ethylene-vinyl acetate), polyacrylate, and polyethylene terephthalate. In one embodiment, said polymer is selected from the group consisting of poly(acrylonitrile-butadiene), poly(ethylene-vinyl acetate), polyacrylate, and polyester. In one embodiment, said polymer is selected from the group consisting of poly(acrylonitrile-butadiene), poly(ethylene-vinyl acetate), polyethylene terephthalate, and polyester. In one embodiment, said polymer is selected from the group consisting of poly(acrylonitrile-butadiene), polyurethane, synthetic polyamide, and polyacrylate. In one embodiment, said polymer is selected from the group consisting of poly(acrylonitrile-butadiene), polyurethane, synthetic polyamide, and polyethylene terephthalate. In one embodiment, said polymer is selected from the group consisting of poly(acrylonitrile-butadiene), polyurethane, synthetic polyamide, and polyester. In one embodiment, said polymer is selected from the group consisting of poly(acrylonitrile-butadiene), polyurethane, polyacrylate, and polyethylene terephthalate. In one embodiment, said polymer is selected from the group consisting of poly(acrylonitrile-butadiene), polyurethane, polyacrylate, and polyester. In one embodiment, said polymer is selected from the group consisting of poly(acrylonitrile-butadiene), polyurethane, polyethylene terephthalate, and polyester. In one embodiment, said polymer is selected from the group consisting of poly(acrylonitrile-butadiene), synthetic polyamide, polyacrylate, and polyethylene terephthalate. In one embodiment, said polymer is selected from the group consisting of poly(acrylonitrile-butadiene), synthetic polyamide, polyacrylate, and polyester. In one embodiment, said polymer is selected from the group consisting of poly(acrylonitrile-butadiene), synthetic polyamide, polyethylene terephthalate, and polyester. In one embodiment, said polymer is selected from the group consisting of poly(acrylonitrile-butadiene), polyacrylate, polyethylene terephthalate, and polyester. In one embodiment, said polymer is selected from the group consisting of poly(acrylonitrile-butadiene), poly(ethylene-vinyl acetate), polyurethane, synthetic polyamide, and polyacrylate. In one embodiment, said polymer is selected from the group consisting of poly(acrylonitrile-butadiene), poly(ethylene-vinyl acetate), polyurethane, synthetic polyamide, and polyethylene terephthalate. In one embodiment, said polymer is selected from the group consisting of poly(acrylonitrile-butadiene), poly(ethylene-vinyl acetate), polyurethane, synthetic polyamide, and polyester. In one embodiment, said polymer is selected from the group consisting of poly (acrylonitrile-butadiene), poly(ethylene-vinyl acetate), polyurethane, polyacrylate, and polyethylene terephthalate. In one embodiment, said polymer is selected from the group consisting of poly(acrylonitrile-butadiene), poly(ethylene-vinyl acetate), polyurethane, polyacrylate, and polyester. In one embodiment, said polymer is selected from the group consisting of poly(acrylonitrile-butadiene), poly(ethylene-vinyl acetate), polyurethane, polyethylene terephthalate, and polyester. In one embodiment, said polymer is selected from the group consisting of poly(acrylonitrile-butadiene), poly (ethylene-vinyl acetate), synthetic polyamide, polyacrylate, and polyethylene terephthalate. In one embodiment, said polymer is selected from the group consisting of poly (acrylonitrile-butadiene), poly(ethylene-vinyl acetate), synthetic polyamide, polyacrylate, and polyester. In one embodiment, said polymer is selected from the group consisting of poly(acrylonitrile-butadiene), poly(ethylene-vinyl acetate), synthetic polyamide, polyethylene terephthalate, and polyester. In one embodiment, said polymer is selected from the group consisting of poly(acrylonitrile-butadiene), poly(ethylene-vinyl acetate), polyacrylate, polyethylene terephthalate, and polyester. In one embodiment, said polymer is selected from the group consisting of poly(acrylonitrile-butadiene), polyurethane, synthetic polyamide, polyacrylate, and polyethylene terephthalate. In one embodiment, said polymer is selected from the group consisting of poly(acrylonitrile-butadiene), polyurethane, synthetic polyamide, polyacrylate, and polyester. In one embodiment, said polymer is selected from the group consisting of poly(acrylonitrile-butadiene), polyurethane, synthetic polyamide, polyethylene terephthalate, and polyester. In one embodiment, said polymer is selected from the group consisting of poly(acrylonitrile-butadiene), polyurethane, polyacrylate, polyethylene terephthalate, and polyester. In one embodiment, said polymer is selected from the group consisting of poly(acrylonitrile-butadiene), synthetic polyamide, polyacrylate, polyethylene terephthalate, and polyester. In one embodiment, said polymer is selected from the group consisting of poly(acrylonitrile-butadiene), poly(ethylene-vinyl acetate), polyurethane, synthetic polyamide, polyacrylate, and polyethylene terephthalate. In one embodiment, said polymer is selected from the group consisting of poly(acrylonitrile-butadiene), poly(ethylene-vinyl acetate), polyurethane, synthetic polyamide, polyacrylate, and polyester. In one embodiment, said polymer is selected from the group consisting of poly(acrylonitrile-butadiene), poly(ethylene-vinyl acetate), polyurethane, synthetic polyamide, polyethylene terephthalate, and polyester. In one embodiment, said polymer is selected from the group consisting of poly(acrylonitrile-butadiene), poly(ethylene-vinyl acetate), polyurethane, polyacrylate, polyethylene terephthalate, and polyester. In one embodiment, said polymer is selected from the group consisting of poly(acrylonitrile-butadiene), poly(ethylene-vinyl acetate), synthetic polyamide, polyacrylate, polyethylene terephthalate, and polyester. In one embodiment, said polymer is selected from the group consisting of poly(acrylonitrile-butadiene), polyurethane, synthetic polyamide, polyacrylate, polyethylene terephthalate, and polyester. In one embodiment, said polymer is selected from the group consisting of poly(acrylonitrile-butadiene), poly(ethylene-vinyl acetate), polyurethane, synthetic polyamide, polyacrylate, polyethylene terephthalate, and polyester.

While the invention has been described with reference to various exemplary aspects and embodiments, it will be understood by those skilled in the art that various changes may be made and equivalents may be substituted for elements thereof without departing from the scope of the invention. Therefore, it is intended that the invention not be limited to any particular embodiment contemplated, but that the invention will include all embodiments falling within the scope of the appended claims. The invention will be further illustrated by the following non-limiting Examples.

REFERENCES

Bombelli et al., 2017, *Curr. Biol.*, 27, 8, R292-R293
Lou et al., 2020, *Environ. Sci. Technol.* 54, 5, 2821-2831

EXAMPLES

Example 1

In this example the larvae of G. mellonella were grown on polypropylene (PP) or beeswax (natural substrate of G. mellonella) and the effect on pupation of different feeding substrates was examined. The calculations were carried out as follows, wherein nb stands for number, and x is given in %:

$$x = \frac{nb(\text{pupae}) - nb(\text{dead})}{\text{initial } nb \text{ larvae}} \times 100$$

Material and Methods

PP (100%) used was from a three-layer surgical face mask (all three layers were used, including non-woven and melt-blown layers), type IIR, manufactured by ESound Med.

The wax used was beeswax from honey provider Asbal.

The larvae were purchased from Vivara (Sweden), at the 6-7th instar, with an average mass of 380 mg.

To avoid any interference the received larvae were starved for two days before the beginning of the differentiate feeding in order to be able to properly appreciate the effect of the newly feed substrate.

28 larvae were placed in square-bottom glass vessels to reach the density of 0.23 larvae per square cm. The temperature was maintained at 25.2+/−1.5° C., and the relative humidity was in the range 35 to 98%.

All the experiments were performed in duplicates and the results are presented as mean values of the two replicative experiments.

Obtained Results and Conclusion

Figure 1:
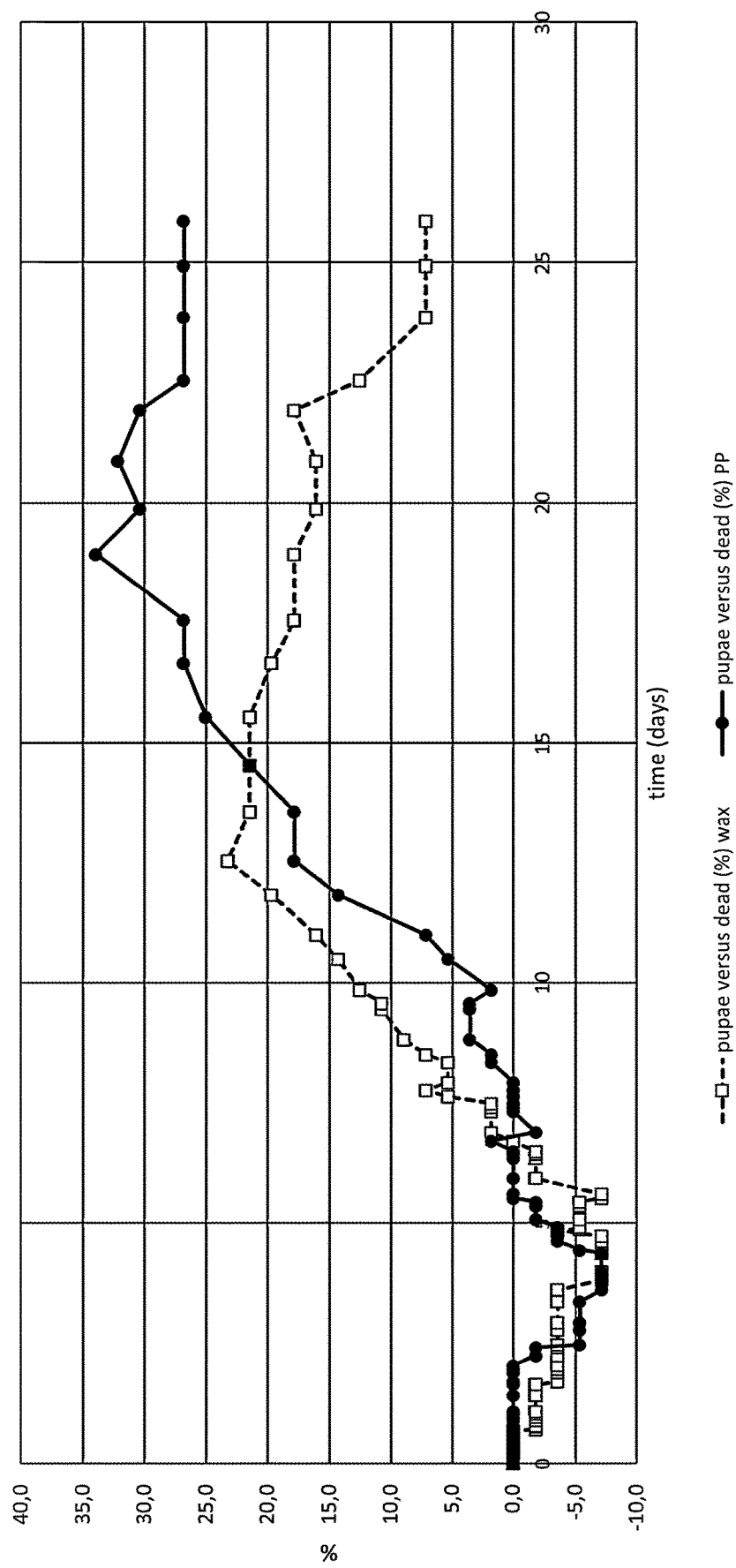
FIG. 1 shows the difference in percentage of the number of pupae versus dead larvae of G. mellonella fed with polypropylene (PP) or with beeswax (wax), in the conditions described in Example 1.

After 17 hours the first deaths among larval population appeared, whereas the first pupae were observed after 4 days of experimentation (FIG. 1). The whole transformation process took more than 3 weeks and can be divided into 3 phases:

first phase—(day 0-7) there are more dead than pupae in both cases;
second phase—second week of the experiment (day 8-14)—in both cases the number of pupae increases significantly faster than the number of dead larvae;
third phase—(day 15-25) the number of dead larvae increases in the wax vessels whereas it remains contained in the PP vessels.

At the end of the experiment, in the vessels that contained wax substrate there was an average of 7.1% of pupae more than dead larvae, whereas in the vessels that contained PP substrate, there was an average of 26.8% more of pupae than dead larvae, that is almost 20% difference between the beeswax and PP substrates.

As can be seen in FIG. 1, an increased pupation for the population of larvae feeding on polypropylene compared to the population of larvae feeding on wax is seen for all tested polymers from the 14$^{th}$ day onwards. At the end of the experiment, after 25 days, the increase of pupation is 27% for the population feed on polypropylene, versus 7% for the population feed on wax.

It can be noted that the relative humidity was in the range 35 to 98%. If the humidity would have been controlled at a favorable range, the present inventor expects that the performance of both populations is expected to be better.

Thus, it was surprisingly found in this experiment that the utilization of polypropylene as feeding substrate is more efficient than the utilization of beeswax for the transformation of larvae into pupae, knowing that wax is the natural feeding substrates for this species. Utilization of polypropylene is very unexpected, especially since polypropylene is certainly more difficult to digest than many other plastic materials, and is highly resistant to chemical degradation. Without being bound by any theory, one reason may be that it lacks functional groups to which a digesting entity (such as for example an enzyme) may bind partially or in whole in order to come into contact with the material to be degraded.

Example 2

In this example the larvae of G. mellonella were grown on different polymers and their mixes, and copolymers, as well as on beeswax. The effect on pupation of different feeding substrates was examined, knowing that wax is the natural feeding substrates for those insects. The calculations were carried out as follows, wherein nb stands for number, and x is given in %:

$$x = \frac{(nb(\text{pupae}) - nb(\text{dead}))\text{susbtrate}}{(\text{initial } nb \text{ larvae})\text{substrate}} \times 100 - \frac{(nb(\text{pupae}) - nb(\text{dead}))\text{wax}}{(\text{initial } nb \text{ larvae})\text{wax}} \times 100$$

Material and Methods

The following materials were used as feed (also referred to as substrate in the calculations above):

Pure Polymers (100%):
  Polyamide (PAm) used was from a sweater manufactured by IPEM (Marseille).
  Polyester (PEster) was from a pyjama manufactured by Lindex.
  Polyacrylate (PAcryl) was coming from a hat manufactured by H&M.
  Cotton was from a sweater manufactured by Benetton.
  Polyethylene (PE) was from a diper packaging manufactured by Libero.

Mixes and Copolymers:
  PAm/polyether-polyurethane copolymer: 82:18, was from a bath cloth manufactured by Medalist;
  PEster/PAm/polyether-polyurethane copolymer: 80:10:10, was from an undercloth manufactured by Man Underwear.
  Paraffin-based wax was from a protection for Bel's group cheese.

To avoid any interference the received larvae were starved for two days before the beginning of the differentiate feeding.

20 larvae were placed in round-bottom glass vessels to reach the density of 1.23 larvae per square cm. The temperature was maintained at 23.9+/−0.6° C., and the relative humidity was maintained at 81.4+/−5.1%. All the experiments were performed in duplicates and the results are presented as mean values of the two replicative experiments.

Obtained Results and Conclusion

Figure 2:
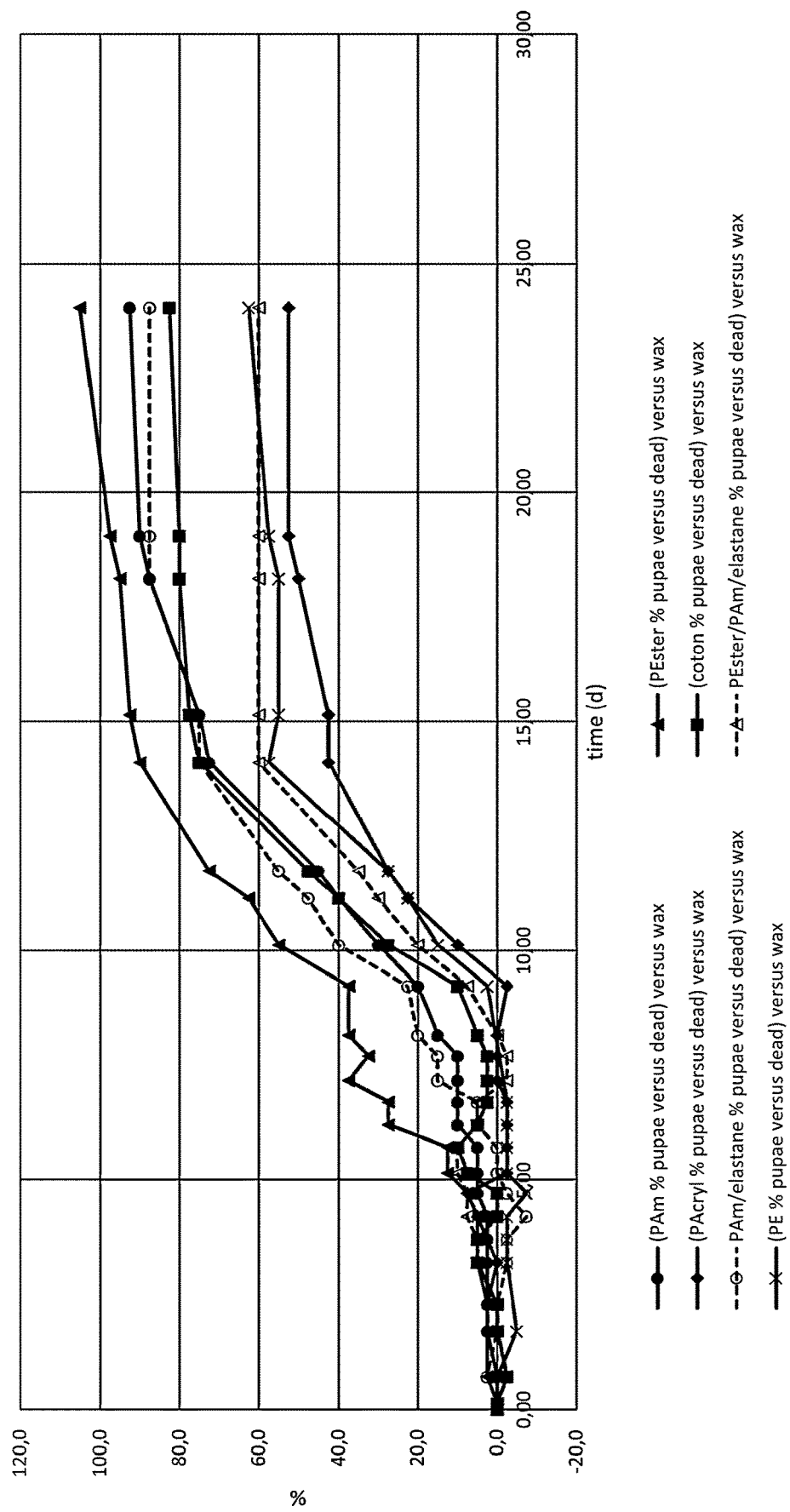
FIG. 2 shows the difference in percentage of the number of pupae versus dead larvae of G. mellonella fed with a polymer feed, versus the difference in percentage of the number of pupae versus dead larvae of G. mellonella fed with beeswax. The conditions and the specific polymers are given in Example 2.
Figure 3:
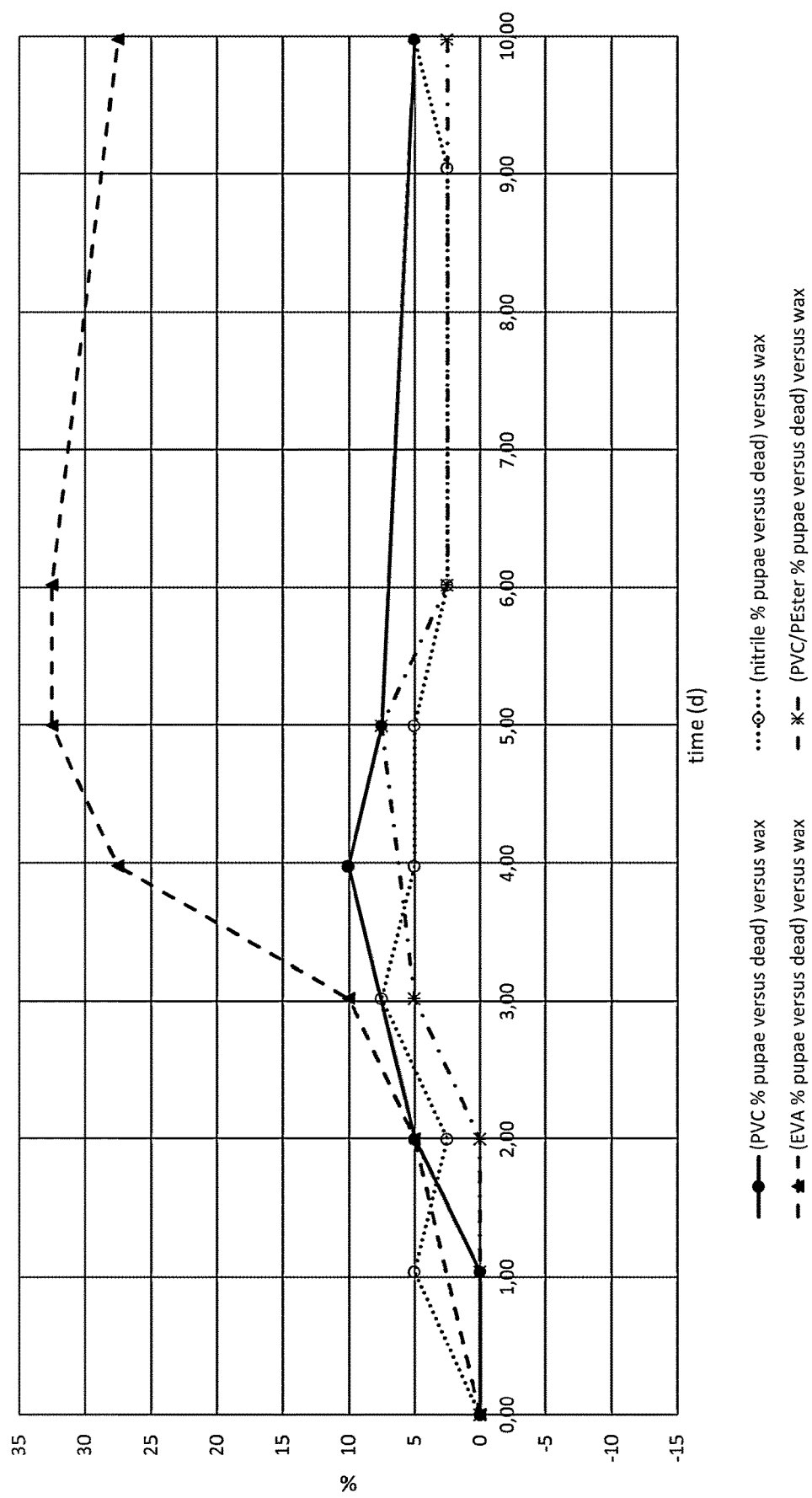
FIG. 3 shows the difference in percentage of the number of pupae versus dead larvae of G. mellonella fed with a polymer feed, versus the difference in percentage of the number of pupae versus dead larvae of G. mellonella fed with beeswax. The conditions and the specific polymers are given in Example 3.

After 17 hours the first dead larvae and pupae among larval population appeared (FIG. 2). The whole transformation process took more than 3 weeks and can be divided into 2 phases:
  first phase, from the beginning of the experiment and up to the 5th to 10th day of the experiment depending on substrate. During the first phase, no significant difference was observed in the the behavior of the larvae and pupae, in other words no significant difference was observed in terms of pupation, for all the feeding substrates as compared to wax;
  second phase, from the 5th to $10^{th}$ day of the experiment and onwards depending on the substate. During the second phase, a clear difference was observed in terms of pupation between the populations fed various plastic polymer substrate and the population fed wax. The results for all the tested polymers, mixes and copolymers lead an increase in pupation in the larval population compared to the larval population fed wax.

In this experiment, the density of larvae was higher than in Example 1 (0.23 vs. 1.23). High larvae density may be avoided due to an increased risk of cannibalism of said larvae. In this experiment, no cannibalism was observed.

At the end of the experiment the difference of the percentage of pupae versus dead comparing to the results in wax is in the range from 52.5% for PAcrylate sample to 97.5% for PEster. The results for the individual materials is shown in Table 1. As can be seen in the table, there is little variation between day 19 and day 24.

TABLE 1

Summary of results at day 19 and day 24 of experiment.
The table summarizes the % increase in pupation between the populations of larvae feed the material as indicated in the table and the control population fed wax.

| Substrate (feed) | % increase in pupation day 19 | % increase in pupation day 24 |
|---|---|---|
| Polyamide (PAm) | 90% | 92.5% |
| Polyester (PEster) | 97.5% | 105% |
| Polyacrylate (PAcryl). | 52.5% | 52.5% |
| Cotton | 80% | 82.5% |
| Polyethylene (PE) | 57% | 62.5% |
| PAm/polyether-polyurethane copolymer: 82:18 | 87.5% | 87.5% |
| PEster/PAm/polyether-polyurethane copolymer: 80:10:10 | 60% | 60% |

As can be seen in FIG. 2, the effect of increased pupation for larvae feeding on the plastic-comprising polymers when compared to the larvae feeding on wax, is seen for all tested polymers from the $9^{th}$ day onwards.

For polyamide (PAm, filled circles), larvae perform better (i.e. the curve is always above zero for this polymer) at all times throughout the experiment compared to larvae fed wax. The largest increment in the graph is seen after 10 to 14 days. After 19 days, the increase of pupation is 90% compared to wax-based feed.

For cotton (filled squares), larvae initially perform at the same level as for wax, better at all times throughout the experiment. The largest increment in the graph is seen after 9 to 14 days. After 19 days, the increase of pupation is 80% compared to wax-based feed.

For polyethylene (PE, cross), larvae initially perform worse than wax, but after 9 days and throughout the experiment, an increase is seen. The largest increment in the graph is seen after 9 to 14 days. After 19 days, the increase of pupation is 57% compared to wax-based feed.

For polyester (PEster, filled triangles), larvae perform better at all times throughout the experiment. The largest increment in the graph is seen after 5 to 14 days. After 19 days, the increase of pupation is 97.5% compared to wax-based feed.

For the mixture of polyamide and elastane (PAm/polyether-polyurethane copolymer, circles on dotted line), larvae initially perform worse than wax, but after 6 days and throughout the experiment, an increase is seen. The largest increment in the graph is seen after 10 to 14 days. After 19 days, the increase of pupation is 87.5% compared to wax-based feed.

For polyacrylate (PAcryl, filled diamonds), larvae initially perform worse or more or less equal to wax, but after 10 days and throughout the experiment, an increase is seen. The largest increment in the graph is seen after 10 to 14 days. After 19 days, the increase of pupation is 52.5% compared to wax-based feed.

For the mixture of polyester, polyamide and elastane (PEster/PAm/polyether-polyurethane copolymer, triangles on dotted line), larvae initially perform better than wax, than worse but close to equal to wax. After 9 days and throughout the experiment an increase is seen. The largest increment in the graph is seen after 9 to 14 days. After 19 days, the increase of pupation is 60% compared to wax-based feed.

Thus, it was surprisingly found in this experiment that the utilization of different polymers, their mixes and copolymers as feeding substrate is more efficient than the utilization of beeswax for the transformation of larvae into pupae, knowing that wax is the natural feeding substrates for those insects.

Example 3

In this example the larvae of G. mellonella were grown on different polymers, their mixes, and copolymers, and on wax. The effect on pupation of different feeding substrates was examined, knowing that wax is the natural feeding substrate for those insects. The calculations were carried out as outlined in Example 2.
Material and Methods
The following materials were used as feed (also referred to as substrate in the calculations above):
Pure Polymers (100%):
  PVC (polyvinyl chloride) was from single use gloves manufactured by Bluewear.
Mixes and Copolymers:
  poly(acrylonitrile-butadiene), hereafter called "nitrile", was from single use gloves PFNBR 243 manufactured by Comfort Rubber Gloves Industries SDN;
  poly(ethylene-vinylacetate), hereafter called "EVA", was from kneepads manufactured by Bluewear;
  PVC/Pester (polyester), 70%/30%, was from gloves manufactured by Bluewear.
Paraffin-Based Wax was from a Protection for Bel's Group Cheese.

The larvae were purchased from Herpers Choise (Sweden), at the 6-7th instar, with an average mass of 320 mg. To avoid any interference the received larvae were starved for two days before the beginning of the differentiate feeding.

20 larvae were placed in square-bottom glass vessels to reach the density of 0.16 larvae per square cm. The temperature was maintained at 23.2+/–0.4 degrees C.

All the experiments were performed in duplicates and the results are presented as mean values of the two replicative experiments.
Obtained Results and Conclusion In all the experiments where the larvae were fed with the polymeric materials the pupation rate is higher than in the experiment conducted with wax.

Figure 6:
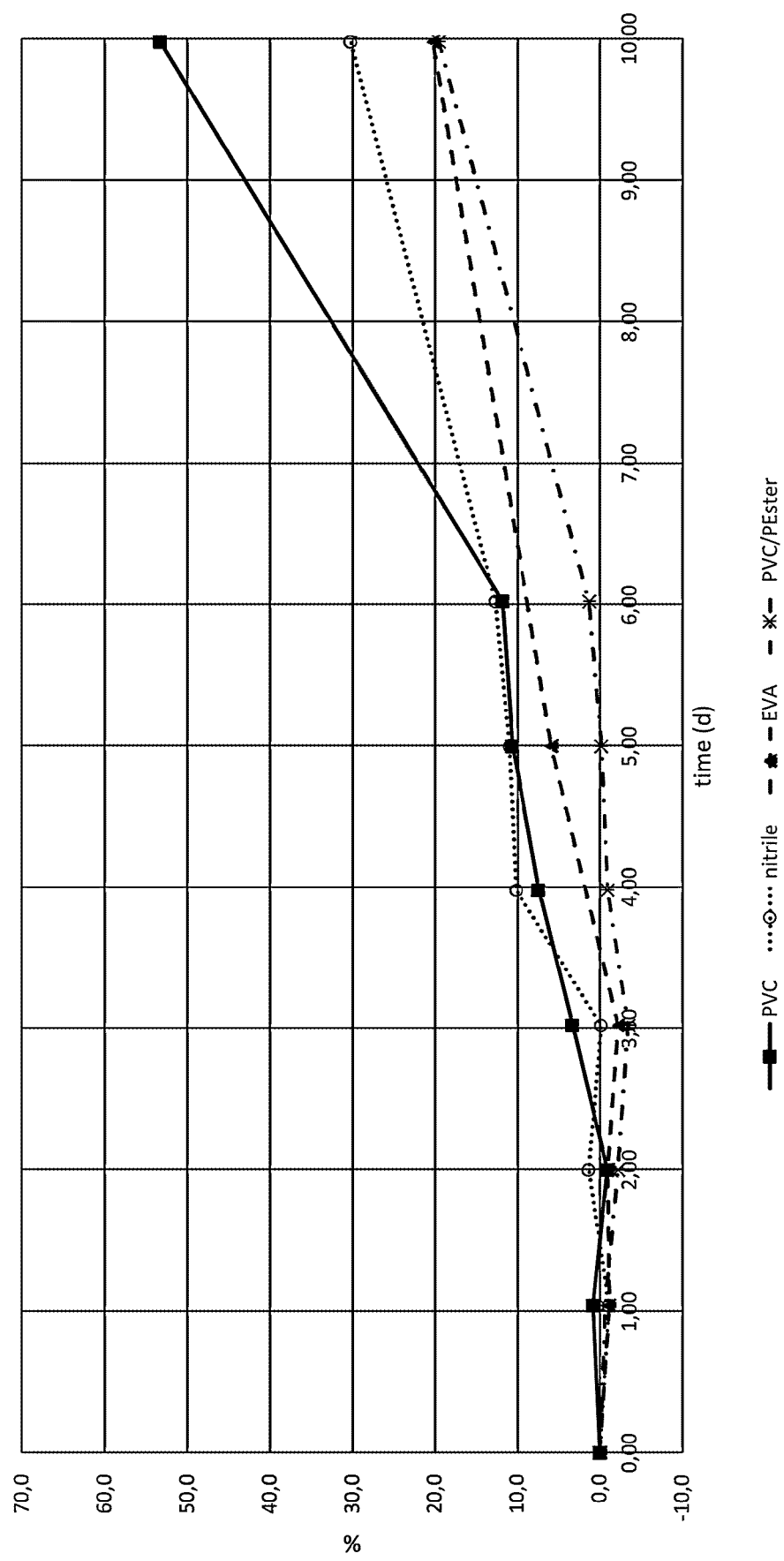
FIG. 6 shows the difference between the mass evolution of larvae, in percentage obtained on a specific feeding substrate with the difference of mass evolution, in percentage, obtained on wax. The conditions and the specific polymers are given in Example 6.

As can be seen in FIG. 6, pupation of larvae feeding on the plastic-comprising polymers when compared to that of the larvae feeding on wax, is increased for all tested polymers from the second day onwards.

For poly(ethylene-vinylacetate) (EVA, triangles), larvae perform better (i.e. the curve is always above zero for this polymer) at all times throughout the experiment compared to larvae fed wax. The largest increment in the graph is seen after 0 to 5 days. After 10 days, the increase of pupation is between 25 and 30% compared to wax-based feed.

For poly(acrylonitrile-butadiene), (nitrile, empty circles), larvae perform better (i.e. the curve is always above zero for this polymer) at all times throughout the experiment compared to larvae fed wax. The largest increment in the graph is seen after 0 to 3 days. After 10 days, the increase of pupation is 5% compared to wax-based feed.

For PVC (filled circles), larvae initially perform at the same level as for wax, and then perform better from the first day onwards throughout the experiment. The largest increment in the graph is seen after 1 to 4 days. After 10 days, the increase of pupation is 5% compared to wax-based feed.

For PVC/PEster (cross), larvae initially perform at the same level as for wax, and then perform better from the second day onwards throughout the experiment. The largest increment in the graph is seen after 2 to 5 days. After 10 days, the increase of pupation is 2.5% compared to wax-based feed.

Thus, it was surprisingly found that the utilization of different types of polymers, their mixes, and copolymers as feeding substrate is more efficient than the utilization of wax for the transformation of larvae into pupae, knowing that wax is the natural feeding substrates for those insects.

Example 4

In this example the larvae of G. mellonella were grown on polypropylene (PP), polyurethane (PUR) and wax and the effect of different feeding substrates on larval mass evolution was examined, knowing that wax is the natural feeding substrates for those insects.

The calculations performed were carried out as follows:

$$x = \frac{(m(l) - m0(l)) \text{susbtrate}}{m0(l) \text{substrate}} \times 100 - \frac{(m(l) - m0(l)) \text{wax}}{m0(l) \text{wax}} \times 100$$

where m(l) stands for average mass of one larva at time t, m0(I) stand for the average initial mass of larva for each respective experiment.
Material and Methods
The Following Materials were Used as Feed (Also Referred to as Substrate in the Calculations Above):
  PP used was from a chocolate packaging, and
  PUR was from a kitchen dishwashing sponge.
  Paraffin-based wax was from a protection for Bel's group cheese.
The larvae were purchased from Vivara (Sweden), at the 6-7th instar, with an average mass of 380 mg.

To avoid any interference the received larvae were starved for two days before being subjected to the different feed in order to be able to properly appreciate the effect of the newly feed substrate.

10 larvae were placed in round-bottom glass vessels to reach the density of 0.63 larvae per square cm. The temperature was maintained at 24.1+/−0.4° C., and the relative humidity was maintained at 78+/−4%.

All the experiments were performed in triplicates and the results are presented as mean values of the three replicative experiments.

Obtained Results and Conclusion

Figure 4:
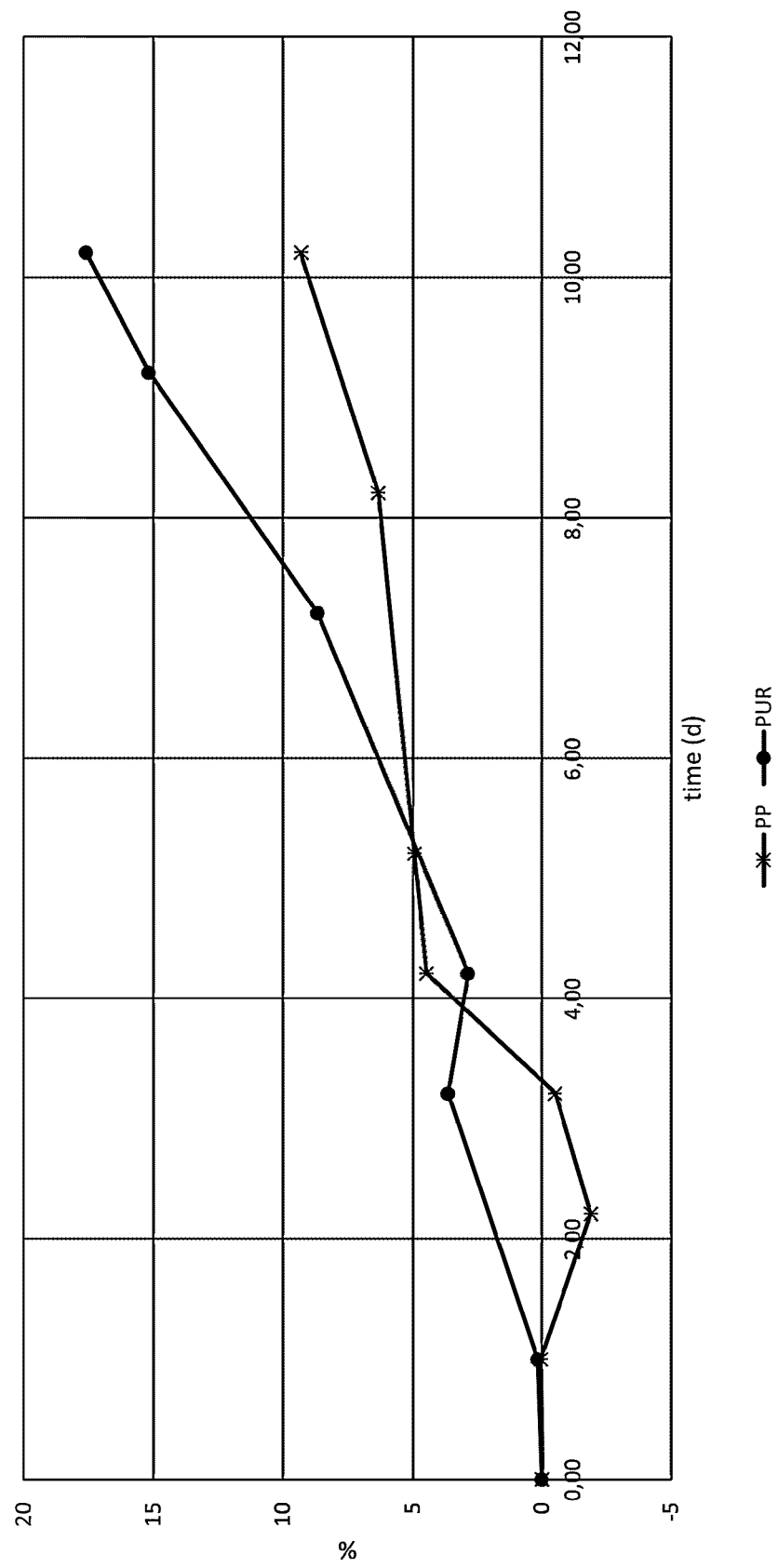
FIG. 4 shows the difference between the mass evolution of larvae in percentage, obtained on PP (cross) and PU (circles) compared to the mass evolution in percentage, obtained on wax. The conditions are described in Example 4.

The experiment lasted for 10 days. During the first 4 days there was an adaptation period of larvae towards the new substrates. The mass evolution was lower with PP substrate comparing to wax during this period (FIG. 4). However, after this adaptation period, the mass of the larvae fed the synthetic substrates increased compared to mass of larvae fed wax, the difference being of 9.3% for PP and 17.6% for PUR at the end of the experiment, knowing that wax is the natural feeding substrates for those insects.

Thus, this experiment establishes that PP and PUR are valuable feeding substrates for studied insects and that feeding the larvae said polymers increases growth and mass of the larvae.

Example 5

In this example the larvae of *G. mellonella* were grown on different polymers, their mixes, and/or copolymers, and on wax and the effect of different feeding substrates on larval mass evolution examined. The calculations were carried out as outlined in Example 4.

Material and Methods

The following materials were used as feed (also referred to as substrate in the calculations above):

Pure Polymers (100%):
  Polyamide (PAm) used was from a sweater manufactured by IPEM (Marseille)
  Polyester (PEster) was from a pyjama manufactured by Lindex
  Polyacrylate (PAcryl) was coming from a hat manufactured by H&M
  Cotton was from a sweater manufactured by Benetton.
Mixes and Copolymers:
  PAm/polyether-polyurethane copolymer: 82:18 was from a bath cloth manufactured by Medalist
  Cotton/polyester/polyether-polyurethane copolymer: 57:38:5 was from an undercloth manufactured by Joliness.

To avoid any interference the received larvae were starved for two days before the beginning of the differentiate feeding.

Paraffin-based wax was from a protection for Bel's group cheese.

20 larvae were placed in round-bottom glass vessels to reach the density of 1.23 larvae per square cm. The temperature was maintained at 23.9+/−0.6° C., and the relative humidity was maintained at 81.4+/−5.1%. All the experiments were performed in duplicates and the results are presented as mean values of the two replicative experiments.

Obtained Results and Conclusion

Figure 5:
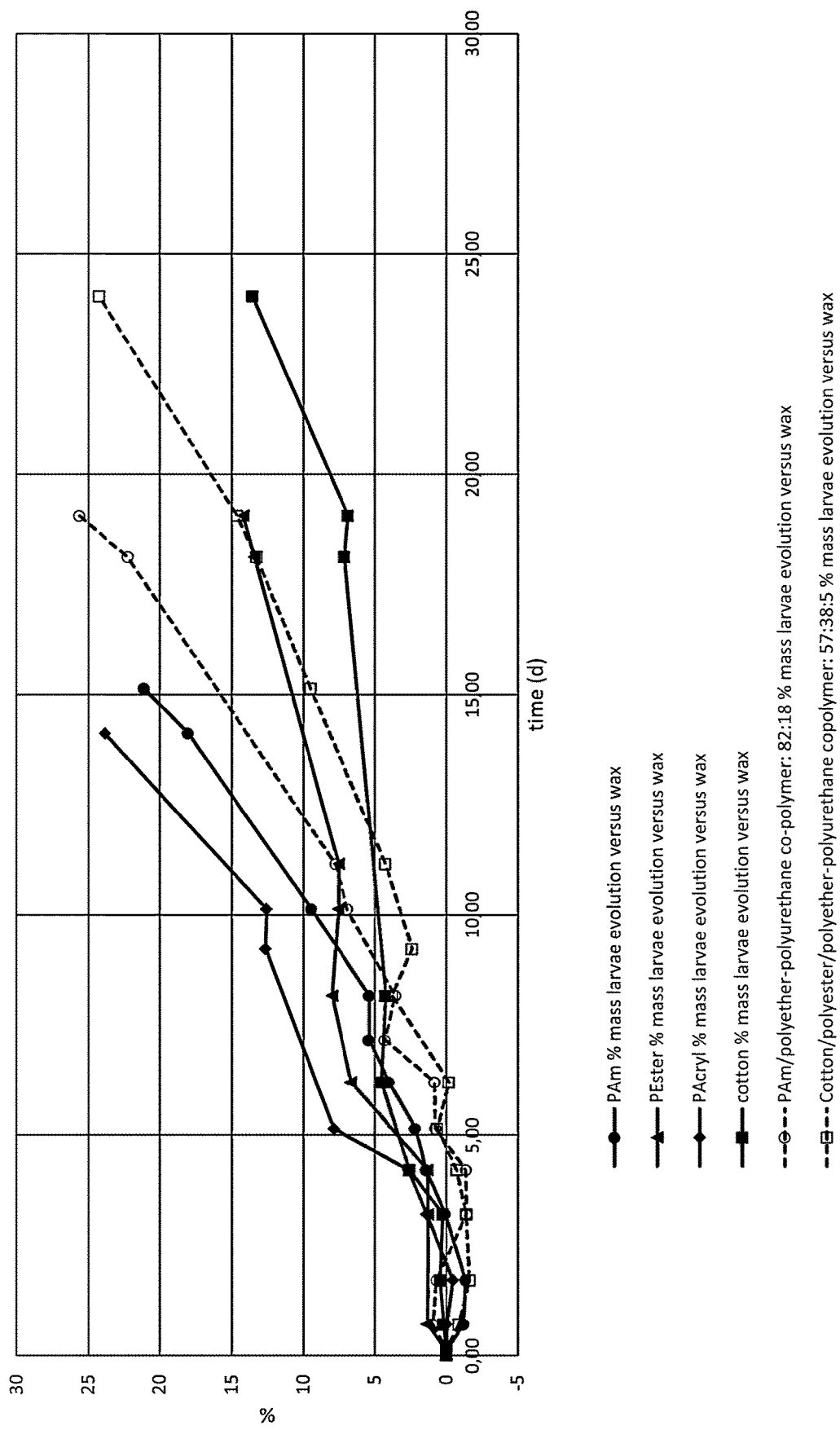
FIG. 5 shows the difference between the mass evolution of larvae, in percentage obtained on a specific feeding substrate with the difference of mass evolution, in percentage, obtained on wax. The conditions and the specific polymers are given in Example 5.

Depending on the substrate the experiment lasted for 14 to 24 days. The individual time point for the end of the experiment is due that that most larvae died of pupated at this point. The obtained results show that there is a need for an adaptation period of 5-6 days for some substrates, e.g., Cotton/polyester/polyether-polyurethane copolymer: 57:38:5, whereas other substrates are directly surperforming comparing to wax, e.g., PAcrylate (FIG. 5). This indicates that the larvae require a period to adapt to a subset of plastic polymer based feeds, while other plastic polymer feeds are immediately efficiently utilized as an energy source for the larvae.

By the end of the experiment all the tested substrates show significant surperformance compared to wax. The mass of larvae fed on the tested plastic polymer feed substrates in significantly increase compared to the mass of larvae fed the wax-based feed, which is the natural feeding substrates for these insect larvae. The data showing the increase in larval mass is summarized in Table 2 below:

TABLE 2

Summary of results at end of experiment. The table summarizes the % increase in larval mass of the populations of larvae feed the material as indicated in the table compared to the control population fed wax.

| Substrate (feed) | End of experiment (day) | % increase in mass |
| --- | --- | --- |
| Polyamide (PAm) | 15 | 21% |
| Polyester (PEster) | 19 | 13% |
| Polyacrylate (PAcryl). | 14 | 24% |
| Cotton | 24 | 13.5% |
| PAm/polyether-polyurethane copolymer: 82:18 | 19 | 25% |
| Cotton/polyester/polyether-polyurethane copolymer: 57:38:5 | 24 | 24% |

Thus, the data indicates that the biomass (as measured by the mass of larvae) increases in the range of from 13% (as shown for PEster) to more than 25% (as shown for PAm/polyether-polyurethane copolymer: 82:18), compared to wax. This is considered a significant increase in the biomass production of the system.

In summary, this experiment establishes that different polymers, their mixes, and copolymers are valuable feeding substrates for studied insects and lead to an increased larval mass compared to natural feed of said insects. It is envisioned that the increase in larval mass may be useful for production of biomass.

Example 6

In this example the larvae of *G. mellonella* were grown on different polymers, their mixes and copolymers, and on wax. The effect of different feeding substrates on larval mass evolution was examined, knowing that wax is the natural feeding substrates for said insects. The calculations were carried out as outlined in Example 4.

Material and Methods

The following materials were used as feed (also referred to as substrate in the calculations above):

Pure Polymers (100%):
  PVC (polyvinyl chloride) was from single use gloves manufactured by Bluewear.
Mixes and Copolymers:
  poly(acrylonitrile-butadiene), hereafter called "nitrile", was from single use gloves PFNBR 243 manufactured by Comfort Rubber Gloves Industries SDN;
  poly(ethylene-vinylacetate), hereafter called "EVA", was from kneepads manufactured by Bluewear;
  PVC/PEster, 70%/30%, was from gloves manufactured by Bluewear.

Paraffin-based wax was from a protection for Bel's group cheese.

The larvae were purchased from Herpers Choise (Sweden), at the 6-7th instar, with an average mass of 320 mg. To avoid any interference the received larvae were starved for two days before the beginning of the differentiate feeding.

20 larvae were placed in square-bottom glass vessels to reach the density of 0.16 larvae per square cm. The temperature was maintained at 23.2+/−0.4 degrees C.

All the experiments were performed in duplicates and the results are presented as mean values of the two replicative experiments.

Obtained Results and Conclusion

The experiment lasted for 10 days. The results are shown in FIG. 6. Two development phases were observed:

The first phase lasted for 2-5 days and corresponds to an adaptation period for the insects, wherein no significant difference between the mass evolution of insects fed with wax and insects fed with different polymeric materials is observed.

In the second phase, when the adaptation is finished, the mass increase of insects fed with polymeric materials is significantly higher in comparison to that of insects fed with wax. After 10 days of experimentation, the mass increase was 20% for EVA and PVC/PEster and 53% for PVC. Thus, the mass increase was in the range of 20-53% for said polymers after 10 days.

Thus, it was surprisingly found that the utilization of different types of polymers, their mixes and copolymers, such as PVC, poly(acrylonitrile-butadiene), EVA and PVC/Pester, are valuable feeding substrates for the studied insects that lead to an increased larval mass compared to natural feed of said insects. It was concluded that valuable feeding substrates for the studied insects comprise copolymers of polyacrylonitrile and polyethylene. It was thus demonstrated that G. mellonella is able to digest a large variety of plastic polymer materials such as pure polymers, polymer mixes and copolymers. It is considered that the increase in larval mass may be useful for production of biomass.

Example 7

In this example the larvae of T. molitor are grown on different polymers, their mixes, and copolymers, and on wheat bran. The effect on pupation of different feeding substrates is examined, knowing that wheat bran is the natural feeding substrates for those insects.

Material and Methods

Pure Polymers (100%):
  Polypropylene (PP) is from a three-layer surgical face mask (all three layers were used, including non-woven and melt-blown layers), type IIR, manufactured by ESound Med;
  Polyamide (PAm) is from a sweater manufactured by IPEM (Marseille), Polyester (PEster) is from a pyjama manufactured by Lindex,
  Polyacrylate (PAcryl) is coming from a hat manufactured by H&M, cotton is from a sweater manufactured by Benetton;
  Polyethylene (PE) is from a dipers' packaging manufactured by Libero Mixes and Copolymers:
  PEster/PAm/polyether-polyurethane copolymer: 80:10:10 is from an undercloth manufactured by Man Underwear;
  Cotton/Polyester/Polyether-polyurethane copolymer: 57:38:5 is from an undercloth manufactured by Joliness To avoid any interference the received larvae are starved for two days before the beginning of the differentiate feeding.

20 larvae are placed in round-bottom glass vessels to reach the density of 1+/−0.5 larvae per square cm. The temperature is maintained at 27+/−2° C., and the relative humidity is maintained at 80+/−5%. All the experiments are performed in duplicates and the results are presented as mean values of the two replicative experiments.

Expected Results and Conclusion

It is expected that larvae need an adaptation period of several days to adjust to the new diets, after this period the pupation rate is expected to be higher in the larval populations fed on the polymers, their mixes, and copolymers that the pupation rate on their natural substrate.

Thus, this experiment is expected to establish that the utilisation of the polymers, their mixes, and copolymers as feeding substrate is more efficient than the utilisation of wheat bran for the transformation of larvae into pupae, knowing that wheat bran is a natural feeding substrates for those insects.

Example 8

In this example the larvae of T. molitor are grown on different polymers, their mixes, and copolymers, and on wheat bran. The effect of different feeding substrates on larval mass evolution is examined, knowing that wheat bran is the natural feeding substrates for those insects.

Material and Methods

Pure Polymers (100%):
  Polypropylene (PP) is from a three-layer surgical face mask (all three layers were used, including non-woven and melt-blown layers), type IIR, manufactured by ESound Med;
  Polyamide (PAm) is from a sweater manufactured by IPEM (Marseille), Polyester (PEster) is from a pyjama manufactured by Lindex,
  Polyacrylate (PAcryl) is coming from a hat manufactured by H&M,
  Cotton is from a sweater manufactured by Benetton;
  Polyethylene (PE) is from a dipers' packaging manufactured by Libero Mixes and Copolymers:
  PEster/PAm/polyether-polyurethane copolymer: 80:10:10 is from an undercloth manufactured by Man Underwear;
  Cotton/polyester/polyether-polyurethane copolymer: 57:38:5 is from an undercloth manufactured by Joliness To avoid any interference the received larvae are starved for two days before the beginning of the differentiate feeding.

20 larvae are placed in round-bottom glass vessels to reach the density of 1+/−0.5 larvae per square cm. The temperature is maintained at 27+/−2° C., and the relative humidity is maintained at 80+/−5%.

All the experiments are performed in duplicates and the results are presented as mean values of the two replicative experiments.

Expected Results and Conclusion

It is expected that larvae need an adaptation period of several days to adjust to the new diets, after this adaptation period the larvae are expected to perform at least as well on the synthetic substrates as on wheat bran.

Thus, this experiment is expected to establish that the polymers, their mixes, and copolymers are valuable feeding substrates for said insects.

Itemized List of Embodiments
1. Use of a feed for producing biomass, said use comprising bringing at least one larva of the family Pyralidae into contact with said feed, wherein said feed comprises at least one plastic polymer, wherein said polymer is selected from the group consisting of polyethylene terephthalate, polypropylene, polyurethane, polyester, polyacrylate, polyglycol, polyvinyl chloride, polycarbonate, polyvinylidene chloride, synthetic polyamide, polypropylene terephthalate and polyether, poly(ethylene-vinylacetate), polyacrylonitrile, and any mixes or copolymers thereof;
   such as a polymer selected from the group consisting of polyethylene terephthalate, polypropylene, polyurethane, polyester, polyacrylate, polyglycol, polyvinyl chloride, polycarbonate, polyvinylidene chloride, synthetic polyamide, polypropylene terephthalate and polyether;
   such as a polymer selected from the group consisting of polyethylene terephthalate, polyurethane, polyester, polyacrylate, polyglycol, polyvinyl chloride, polycarbonate, polyvinylidene chloride, synthetic polyamide, polypropylene terephthalate and polyether;
   such as a polymer selected from the group consisting of synthetic polyamide; polyacrylate; a mixture of synthetic polyamide and a copolymer of polyether-polyurethane; polyester; cotton; a mixture of polyester, synthetic polyamide and copolymer of polyether-polyurethane; polyethylene; and poly(ethylene-vinylacetate);
   such as a polymer selected from the group consisting of synthetic polyamide; a mixture of synthetic polyamide and a copolymer of polyether-polyurethane; polyester; and poly(ethylene-vinylacetate);
   such as a polymer selected from the group consisting of synthetic polyamide; polyester; and poly(ethylene-vinylacetate);
   allowing said at least one larva to feed on said at least one plastic polymer, thereby
   producing biomass.
2. Use according to item 1, wherein said feed consists of said at least one plastic polymer, wherein said polymer is selected from the group consisting of polyethylene terephthalate, polypropylene, polyurethane, polyester, polyacrylate, polyglycol, polyvinyl chloride, polycarbonate, polyvinylidene chloride, synthetic polyamide, and any mixes or copolymers thereof.
3. Use according to any one of items 1 to 2, wherein said polymer is selected from the group consisting of polyethylene terephthalate, polypropylene, polyurethane, synthetic polyamide, polyester, polyacrylate, polyether and any mixes or copolymers thereof.
4. Use according to any one of items 1 to 3, wherein said polymer is selected from the group consisting of polypropylene, polyurethane, synthetic polyamide, polyester, and any mixes or copolymers thereof.
5. Use according to any one of items 1 to 3, wherein said polymer is selected from the group consisting of polypropylene, polyurethane, synthetic polyamide and polyacrylate, and any mixes or copolymers thereof.
6. Use according to any one of items 1 to 3, wherein said polymer is a mixture of synthetic polyamide and a polyether-polyurethane copolymer.
7. Use according to any one of items 1 to 3 and 5, said polymer is selected from the group consisting of polypropylene, polyurethane, and polyacrylate, and any mixes or copolymers thereof.
8. Use according to any one of items 1 to 3, wherein said polymer is selected from the group consisting of polypropylene, and polyethylene terephthalate, and any mixes or copolymers thereof.
9. Use according to any one of items 1 to 3, wherein said polymer is selected from the group consisting of polypropylene, synthetic polyamide, polyacrylate, and polyester and any mixes or copolymers thereof.
10. Use according to any one of items 1 to 5 and 7, wherein said polymer is selected from the group consisting of polypropylene and polyurethane, and any mixes or copolymers thereof.
11. Use according to any one of items 1 to 2, wherein said copolymer comprises at least two polymers, independently selected from the group consisting of polyethylene terephthalate, polypropylene, polyurethane, polyester, polyacrylate, polyether, polyglycol, polyvinyl chloride, polycarbonate, and polyvinylidene chloride.
12. Use according to any one of items 1 to 11, wherein said copolymer comprises at least two polymers, independently selected from the group consisting of polyether, polypropylene, and polyurethane, and optionally wherein said copolymer further comprises a polymer selected from the group consisting of synthetic polyamide and polyester, or any mixes thereof.
13. Use according to any one of items 11 to 12, wherein said copolymer is a polyether-polyurethane copolymer, such as elastane.
14. Use according to any one of items 11 to 13, wherein said copolymer further comprises an additional polymer.
15. Use according to any one of items 11 to 14, wherein said copolymer further comprises a polymer selected from the group consisting of polyethylene, synthetic polyamide and a polysaccharide such as cellulose, or any mixes thereof.
16. Use according to any one of items 11 to 14, wherein said copolymer further comprises a polymer selected from the group consisting of synthetic polyamide, polyester, polyacryl, polyethylene and cellulose.
17. Use according to any one of items 1 to 4, 9, 11, and 15 to 16, wherein said polyester is selected from the group consisting of polyethylene terephthalate, polypropylene terephthalate, polycaprolactone, and polyethylene adipate.
18. Use according to any one of items 1 to 6, 9, 12, and 15 to 16, wherein said synthetic polyamide is selected from the group consisting of PA 6; PA 6.6; PA 10 and PA 12.
19. Use according to any one of the preceding items, wherein said use exhibits an increase in pupation in a population of said larva compared to when a corresponding population of larva is fed a natural feed for said larva, such as a wax-based feed.
20. Use of a feed for increasing pupation in a population of larva of the family Pyralidae, the use comprising
   bringing said population into contact with said feed and allowing the population to feed on said feed, wherein said feed comprises at least one polymer, wherein said polymer is selected from the group consisting of polyethylene, polyethylene terephthalate, polypropylene, polyurethane, polyester, polyacrylate, polyglycol, polyvinyl chloride, polycarbonate, polyvinylidene chloride, synthetic polyamide, polypropylene terephthalate and polyether, poly(ethylene-vinylacetate), polyacrylonitrile, and any mixes or copolymers thereof;

such as a polymer selected from the group consisting of polyethylene, polyethylene terephthalate, polypropylene, polyurethane, polyamide, polyester, polyacrylate, polystyrene, polyether, polyglycol, polysaccharide, polyvinyl chloride, polycarbonate, polyvinylidene chloride, and any mixes or copolymers thereof;

such as a polymer selected from the group consisting of polyethylene terephthalate, polypropylene, polyurethane, polyester, polyacrylate, polyglycol, polyvinyl chloride, polycarbonate, polyvinylidene chloride, synthetic polyamide, polypropylene terephthalate and polyether;

such as a polymer is selected from the group consisting of synthetic polyamide; polyacrylate; a mixture of synthetic polyamide and a copolymer of polyether-polyurethane; polyethylene; polyester; cotton; a mixture of polyester, synthetic polyamide and copolymer of polyether-polyurethane; polyethylene; and poly(ethylene-vinylacetate);

such as a polymer is selected from the group consisting of synthetic polyamide; a mixture of synthetic polyamide and a copolymer of polyether-polyurethane; polyethylene; polyester; and poly(ethylene-vinylacetate);

such as a polymer is selected from the group consisting of synthetic polyamide; polyester; and poly(ethylene-vinylacetate); and wherein said pupation is increased compared to when a corresponding population is fed a natural feed for said larva, such as a wax-based feed.

21. Use according to item 20, wherein said feed consists of at least one plastic polymer, wherein said polymer is selected from the group consisting of polyethylene, polyethylene terephthalate, polypropylene, polyurethane, polyamide, polyester, polyacrylate, polystyrene, polyether, polyglycol, polysaccharide, polyvinyl chloride, polycarbonate, polyvinylidene chloride, and any mixes or copolymers thereof.

22. Use according to item 20 or 21, wherein said wax-based feed is beeswax.

23. Use according to any one of items 20 to 22 wherein said polymer is selected from the group consisting of polyethylene; polypropylene; polyurethane; polyamide; polyester; polyacrylate; polystyrene; polyether, such as cellulose; and any mixes or copolymers thereof.

24. Use according to any one of items 20 to 23, wherein said polymer is selected from the group consisting of polyethylene, polypropylene, polyurethane, polyamide, polyester, and any mixes or copolymers thereof.

25. Use according to any one of items 20 to 23, wherein said polymer is selected from the group consisting of polypropylene, polyurethane, polyamide and polyacrylate, and any mixes or copolymers thereof.

26. Use according to any one of items 20 to 23, wherein said polymer is selected from the group consisting of polyester; polyamide; polyether, such as cellulose; or a mixture of polyamide and a polyether-polyurethane copolymer.

27. Use according to any one of items 20 to 23 and 25, wherein said polymer is selected from the group consisting of polypropylene, polyurethane, and polyacrylate, and any mixes or copolymers thereof.

28. Use according to any one of items 20 to 23, wherein said polymer is selected from the group consisting of polypropylene, polyethylene, and polystyrene, and any mixes or copolymers thereof.

29. Use according to any one of items 20 to 23, wherein said polymer is selected from the group consisting of polypropylene, polyamide, polyacrylate, polyester, and polyether, and any mixes or copolymers thereof.

30. Use according to any one of items 20 to 22 and 29, wherein said polyether is a polysaccharide.

31. Use according to item 30, wherein said polysaccharide is cellulose.

32. Use according to item 31, wherein said cellulose is cotton.

33. Use according to any one of items 20 to 24, wherein said polymer is selected from the group consisting of polypropylene, polyethylene, and polyurethane, and any mixes or copolymers thereof.

34. Use according to any one of items 20 to 25, 27 and 33, wherein said polymer is selected from the group consisting of polypropylene and polyurethane, and any mixes or copolymers thereof.

35. Use according to anyone of items 20 to 34, wherein said polymer is a synthetic polymer.

36. Use according to any one of items 20 to 24, and 28, wherein said polyester is selected from the group consisting of polyethylene terephthalate, polypropylene terephthalate, polycaprolactone, and polyethylene adipate.

37. Use according to any one of items 20 to 26, and 29, wherein said polyamide is selected from the group consisting of PA 6, PA 6.6, PA 10 and PA 12.

38. Use according to any one of items 20 to 37, wherein said wax-based feed comprises approximately at maximum 10%, such as approximately at maximum 5%, such as approximately at maximum 3%, such as approximately at maximum 1% by weight of a polymer selected from the group consisting of polyethylene, polyethylene terephthalate, polypropylene, polyurethane, polyamide, polyester, polyacrylate, polystyrene, polyether, polyglycol, polysaccharide, cellulose, polyvinyl chloride, polycarbonate, polyvinylidene chloride, and any mixes or copolymers thereof.

39. Use according to any one of items 20 to 38, wherein said increase of pupation is quantified as the difference between the number of pupae versus dead larvae compared to the initial number of larvae in said population.

40. Use according to any one of items 20 to 39, wherein said increase of pupation is after at least 4 days, such as at least 5 days, such as at least 6 days, such as at least 7 days, such as at least 8 days, such as at least 9 days, such as at least 10 days, such as at least 11 days, such as at least 12 days, such as at least 13 days, such as at least 14 days, such as at least 15 days, such as at least 16 days, such as at least 17 days, such as at least 18 days, such as at least 19 days, such as at least 20 days, such as at least 21 days, such as at least 22 days, such as at least 23 days, such as at least 24 days, such as at least 25 days, such as at least 26 days, such as at least 27 days, such as at least 28 days, such as at least 29 days, such as at least 30 days, such as at least 35 days, such as at least 40 days.

41. Use according to any ones of items 20 to 40, wherein said increase of pupation is approximately at least 5%, such as approximately at least 7%, such as approximately at least 10%, such as approximately at least 15%, such as approximately at least 20%, such as approximately at least 25%, such as approximately at least 30%, such as approximately at least 40%, such as approximately at least 50%, such as approximately at least 60%, such as approximately at least 70%, such as approximately at least 80%, such as approximately at least 90%, such as approximately at least 100%.

42. Use according to any ones of items 20 to 41, wherein said increase of pupation is within the range of 5 to 50%, such as within the range of 10 to 35%, such as within the range of 15 to 25%, such as within the range of 18 to 22%, such as around 20%.
43. Use according to any one of the preceding items, wherein said biomass comprises pupae of the family Pyralidae, and/or larvae of the family Pyralidae, and/or feces of said larvae.
44. Use according to item 43, wherein said biomass comprises pupae of the family Pyralidae.
45. Use according to item 43, wherein said biomass comprises larvae of the family Pyralidae.
46. Use according to item 43, wherein said biomass comprises feces of said larvae of the family Pyralidae.
47. Use according to items 44 to 47, wherein said biomass further comprises polyethylene glycol.
48. Use according to any one of the preceding items, wherein said biomass is harvested after at least 5 days, such as 10 days, such as 15 days, such as 16 days, such as 17 days, such as 18 days, such as 19 days, such as 20 days, such as 21 days, such as 22 days, such as 23 days, such as 24 days, such as 25 days, such as 30 days, such as 35 days, such as 40 days, such as 45 days.
49. Use of a feed for producing biomass according to any one of items 1-48, wherein said use is a continuous use, which use comprises the steps of
a) providing a population of larvae B,
b) bringing said population into contact with said feed as defined in any one of items 1 to 18, 20 to 21 and 23 to 37 and allowing said population to feed on said feed,
c) allowing an amount A of B to develop into pupae, and harvesting biomass comprising an amount (B-A) larvae,
d) allowing said pupae to transform into moths, and
e) allowing said moths to produce larvae, thereby obtaining a population of larvae B', and
repeating steps a) to e).
50. Use according to item 49, wherein said use does not require external addition of larvae.
51. Use according to any one of items 49 to 50, wherein said population of larvae B' is maintained at approximate ±1% of B, such as ±approximate 2% of B, such as ±approximate 3% of B, such as ±approximate 4% of B, such as ±approximate 5% of B, such as ±approximate 6% of B, such as ±approximate 7% of B, such as ±approximate 8% of B, such as ±approximate 9% of B, such as ±approximate 10% of B, such as ±approximate 11% of B, such as ±approximate 12% of B, such as ±approximate 13% of B, such as ±approximate 14% of B, such as ±approximate 15% of B, such as ±approximate 20% of B, such as ±approximate 25% of B.
52. Use according to any one of items 49 to 51, wherein said amount A is approximate 0.5% of B, such as approximate 1% of B, such as approximate 2% of B, such as approximate 3% of B, such as approximate 4% of B, such as approximate 5% of B, such as approximate 6% of B, such as approximate 7% of B, such as approximate 8% of B, such as approximate 9% of B, such as approximate 10% of B, such as approximate 11% of B, such as approximate 12% of B, such as approximate 13% of B, such as approximate 14% of B, such as approximate 15% of B, such as approximate 16% of B, such as approximate 17% of B, such as approximate 18% of B, such as approximate 19% of B, such as approximate 20% of B, such as approximate 25% of B, such as approximate 30% of B, such as approximate 35% of B, such as approximate 40% of B, such as approximate 45% of B, such as approximate 50% of B.
53. Use according to any one of the preceding items, wherein said at least one larva of the family Pyralidae is selected from the group consisting of *Galleria mellonella* and *Achroia grisella*.
54. Use according to any one items 1 to 52, wherein said at least one larva of the family Pyralidae is selected from the group consisting of *Galleria austrina, Galleria cerea, Galleria cerealis, Galleria cereana, Galleria cerella, Galleria crombrugcheela, Galleria obliquella*, and *Galleria mellonella*, such as wherein said at least one larva of the family Pyralidae is *Galleria mellonella*.
55. Use according any one of the preceding items, wherein said use is performed in a closed system.
56. Use according any one of the preceding items, wherein said larvae are brought into contact with said feed in a container.
57. Use according to item 56, wherein said container is made of glass, metals, metal alloys, composites, or treated wood, and any mixes thereof.
58. Use according any one of the preceding items, wherein said use is performed at a temperature of from 4° C. to 40° ° C., such as from 15° C. to 35° C., preferably of from 20° C. to 30° C., most preferably of from 25° C. to 27° C.
59. Use according any one of the preceding items, wherein said use is at a humidity of from 30% to 99%.
60. Use according to item 59, wherein said humidity is maintained at 80.0+/−5%.
61. Use according any one of the preceding items, wherein said larva is subjected to starvation prior to adding any feed.
62. Use according to item 61, wherein said starvation is for 1 to 20 days, such as for 1 to 10, such as for 1 to 5 days, such as for 2 days.
63. Method for producing biomass, the method comprising bringing at least one larva of the family Pyralidae or of the family Tenebrionidae into contact with a feed, wherein said feed comprises at least one plastic polymer, wherein said polymer is selected from the group consisting of polyethylene terephthalate, polypropylene, polyurethane, polyester, polyacrylate, polyglycol, polyvinyl chloride, polycarbonate, polyvinylidene chloride, synthetic polyamide, polypropylene terephthalate and polyether, poly(ethylene-vinylacetate), polyacrylonitrile, and any mixes or copolymers thereof;
such as a polymer is selected from the group consisting of polyethylene terephthalate, polypropylene, polyurethane, polyester, polyacrylate, polyglycol, polyvinyl chloride, polycarbonate, polyvinylidene chloride, synthetic polyamide, polypropylene terephthalate and polyether;
such as a polymer selected from the group consisting of polyethylene terephthalate, polyurethane, polyester, polyacrylate, polyglycol, polyvinyl chloride, polycarbonate, polyvinylidene chloride, synthetic polyamide, polypropylene terephthalate and polyether;
such as a polymer is selected from the group consisting of synthetic polyamide; polyacrylate; a mixture of synthetic polyamide and a copolymer of polyether-polyurethane; polyester; cotton; a mixture of polyester, synthetic polyamide and copolymer of polyether-polyurethane; and poly(ethylene-vinylacetate);

such as a polymer is selected from the group consisting of synthetic polyamide; a mixture of synthetic polyamide and a copolymer of polyether-polyurethane; polyester; and poly(ethylene-vinylacetate);

such as a polymer is selected from the group consisting of synthetic polyamide; polyester; and poly(ethylene-vinylacetate);

allowing said at least one larva to feed on said at least one plastic polymer, thereby producing biomass.

64. Method according to item 63, wherein said feed consists of said at least one plastic polymer, wherein said polymer is selected from the group consisting of polyethylene terephthalate, polypropylene, polyurethane, polyester, polyacrylate, polyglycol, polyvinyl chloride, polycarbonate, polyvinylidene chloride, synthetic polyamide, and any mixes or copolymers thereof.

65. Method according to any one of items 63 to 64, wherein said polymer is selected from the group consisting of polyethylene terephthalate, polypropylene, polyurethane, synthetic polyamide, polyester, polyacrylate, polyether and any mixes or copolymers thereof.

66. Method according to any one of items 63 to 65, wherein said polymer is selected from the group consisting of polypropylene, polyurethane, synthetic polyamide, polyester, and any mixes or copolymers thereof.

67. Method according to any one of items 63 to 66, wherein said polymer is selected from the group consisting of polypropylene, polyurethane, synthetic polyamide and polyacrylate, and any mixes or copolymers thereof.

68. Method according to any one of items 63 to 65, wherein said polymer is a mixture of synthetic polyamide and a polyether-polyurethane co-polymer.

69. Method according to any one of items 63 to 65 and 67, said polymer is selected from the group consisting of polypropylene, polyurethane, and polyacrylate, and any mixes or copolymers thereof.

70. Method according to any one of items 63 to 65, wherein said polymer is selected from the group consisting of polypropylene, and polyethylene terephthalate, and any mixes or copolymers thereof.

71. Method according to any one of items 63 to 65, wherein said polymer is selected from the group consisting of polypropylene, synthetic polyamide, polyacrylate, and polyester and any mixes or copolymers thereof.

72. Method according to any one of items 63 to 67 and 69, wherein said polymer is selected from the group consisting of polypropylene and polyurethane, and any mixes or copolymers thereof.

73. Method according to any one of items 63 to 64, wherein said co-polymer comprises at least two polymers, independently selected from the group consisting of polyethylene terephthalate, polypropylene, polyurethane, polyester, polyacrylate, polyether, polyglycol, polyvinyl chloride, polycarbonate, and polyvinylidene chloride.

74. Method according to any one of items 63 to 73, wherein said co-polymer comprises at least two polymers, independently selected from the group consisting of polyether, polypropylene, and polyurethane, and optionally wherein said co-polymer further comprises a polymer selected from the group consisting of synthetic polyamide and polyester, or any mixes thereof.

75. Method according to any one of items 73 to 74, wherein said co-polymer is a polyether-polyurethane co-polymer, such as elastane.

76. Method according to any one of items 73 to 75, wherein said co-polymer further comprises an additional polymer.

77. Method according to any one of items 73 to 76, wherein said co-polymer further comprises a polymer selected from the group consisting of polyethylene, synthetic polyamide and a polysaccharide such as cellulose, or any mixes thereof.

78. Method according to any one of items 73 to 76, wherein said co-polymer further comprises a polymer selected from the group consisting of synthetic polyamide, polyester, polyacryl, polyethylene and cellulose.

79. Method according to any one of items 63 to 66, 71, 73, and 77 to 78, wherein said polyester is selected from the group consisting of polyethylene terephthalate, polypropylene terephthalate, polycaprolactone, and polyethylene adipate.

80. Method according to any one of items 63 to 68, 71, 74, and 77 to 78, wherein said synthetic polyamide is selected from the group consisting of PA 6; PA 6.6; PA 10 and PA 12.

81. Method according to any one of items 63 to 80, wherein said method exhibits an increase in pupation in a population of said larva compared to when a corresponding population of larva is fed a natural feed for said larva, such as a wax-based feed.

82. Method for increasing pupation in a population of larva of the family Pyralidae, the method comprising bringing said population into contact with feed and allowing the population to feed on said feed, wherein said feed comprises at least one polymer, wherein said polymer is selected from the group consisting of polyethylene, polyethylene terephthalate, polypropylene, polyurethane, polyester, chloride, synthetic polyamide, polypropylene terephthalate and polyether, poly(ethylene-vinylacetate), polyacrylonitrile, and any mixes or copolymers thereof;

such as a polymer selected from the group consisting of polyethylene, polyethylene terephthalate, polypropylene, polyurethane, polyamide, polyester, polyacrylate, polystyrene, polyether, polyglycol, polysaccharide, polyvinyl chloride, polycarbonate, polyvinylidene chloride, and any mixes or copolymers thereof;

such as a polymer selected from the group consisting of polyethylene terephthalate, polypropylene, polyurethane, polyester, polyacrylate, polyglycol, polyvinyl chloride, polycarbonate, polyvinylidene chloride, synthetic polyamide, polypropylene terephthalate and polyether;

such as a polymer is selected from the group consisting of synthetic polyamide; polyacrylate; a mixture of synthetic polyamide and a copolymer of polyether-polyurethane; polyethylene; polyester; cotton; a mixture of polyester, synthetic polyamide and copolymer of polyether-polyurethane; polyethylene; and poly(ethylene-vinylacetate);

such as a polymer is selected from the group consisting of synthetic polyamide; a mixture of synthetic polyamide and a copolymer of polyether-polyurethane; polyethylene; polyester; and poly(ethylene-vinylacetate);

such as a polymer is selected from the group consisting of synthetic polyamide; polyester; and poly(ethylene-vinylacetate);

and
wherein said pupation is increased compared to when a corresponding population is fed a natural feed for said larva, such as a wax-based feed.

83. Method according to item 82, wherein said feed consists of at least one plastic polymer, wherein said polymer is selected from the group consisting of polyethylene, polyethylene terephthalate, polypropylene, polyurethane, polyamide, polyester, polyacrylate, polystyrene, polyether, polyglycol, polysaccharide, polyvinyl chloride, polycarbonate, polyvinylidene chloride, and any mixes or copolymers thereof.

84. Method according to item 82 or 83, wherein said wax-based feed is beeswax.

85. Method according to any one of items 82 to 84 wherein said polymer is selected from the group consisting of polyethylene; polypropylene; polyurethane; polyamide; polyester; polyacrylate; polystyrene; polyether, such as cellulose; and any mixes or copolymers thereof.

86. Method according to any one of items 82 to 85, wherein said polymer is selected from the group consisting of polyethylene, polypropylene, polyurethane, polyamide, polyester, and any mixes or copolymers thereof.

87. Method according to any one of items 82 to 85, wherein said polymer is selected from the group consisting of polypropylene, polyurethane, polyamide and polyacrylate, and any mixes or copolymers thereof.

88. Method according to any one of items 82 to 85, wherein said polymer is selected from the group consisting of polyester; polyamide; polyether, such as cellulose; or a mixture of polyamide and a polyether-polyurethane co-polymer.

89. Method according to any one of items 82 to 85 and 87, wherein said polymer is selected from the group consisting of polypropylene, polyurethane, and polyacrylate, and any mixes or copolymers thereof.

90. Method according to any one of items 82 to 85, wherein said polymer is selected from the group consisting of polypropylene, polyethylene, and polystyrene, and any mixes or copolymers thereof.

91. Method according to any one of items 82 to 85, wherein said polymer is selected from the group consisting of polypropylene, polyamide, polyacrylate, polyester, and polyether, and any mixes or copolymers thereof.

92. Method according to any one of items 82 to 84 and 91, wherein said polyether is a polysaccharide.

93. Method according to item 92, wherein said polysaccharide is cellulose.

94. Method according to item 93, wherein said cellulose is cotton.

95. Method according to any one of items 82 to 86, wherein said polymer is selected from the group consisting of polypropylene, polyethylene, and polyurethane, and any mixes or copolymers thereof.

96. Method according to any one of items 82 to 85, 89 and 95, wherein said polymer is selected from the group consisting of polypropylene and polyurethane, and any mixes or copolymers thereof.

97. Method according to anyone of items 82 to 96, wherein said polymer is a synthetic polymer.

98. Method according to any one of items 82 to 86, and 90, wherein said polyester is selected from the group consisting of polyethylene terephthalate, polypropylene terephthalate, polycaprolactone, and polyethylene adipate.

99. Method according to any one of items 82 to 88, and 91, wherein said polyamide is selected from the group consisting of PA 6, PA 6.6, PA 10 and PA 12.

100. Method according to any one of items 82 to 99, wherein said wax-based feed comprises approximately at maximum 10%, such as approximately at maximum 5%, such as approximately at maximum 3%, such as approximately at maximum 1% by weight of a polymer selected from the group consisting of polyethylene, polyethylene terephthalate, polypropylene, polyurethane, polyamide, polyester, polyacrylate, polystyrene, polyether, polyglycol, polysaccharide, cellulose, polyvinyl chloride, polycarbonate, polyvinylidene chloride, and any mixes or copolymers thereof.

101. Method according to any one of items 82 to 100, wherein said increase of pupation is quantified as the difference between the number of pupae versus dead larvae compared to the initial number of larvae in said population.

102. Method according to any one of items 82 to 101, wherein said increase of pupation is after at least 4 days, such as at least 5 days, such as at least 6 days, such as at least 7 days, such as at least 8 days, such as at least 9 days, such as at least 10 days, such as at least 11 days, such as at least 12 days, such as at least 13 days, such as at least 14 days, such as at least 15 days, such as at least 16 days, such as at least 17 days, such as at least 18 days, such as at least 19 days, such as at least 20 days, such as at least 21 days, such as at least 22 days, such as at least 23 days, such as at least 24 days, such as at least 25 days, such as at least 26 days, such as at least 27 days, such as at least 28 days, such as at least 29 days, such as at least 30 days, such as at least 35 days, such as at least 40 days.

103. Method according to any ones of items 82 to 102, wherein said increase of pupation is approximately at least 5%, such as approximately at least 7%, such as approximately at least 10%, such as approximately at least 15%, such as approximately at least 20%, such as approximately at least 25%, such as approximately at least 30%, such as approximately at least 40%, such as approximately at least 50%, such as approximately at least 60%, such as approximately at least 70%, such as approximately at least 80%, such as approximately at least 90%, such as approximately at least 100%.

104. Method according to any ones of items 82 to 103, wherein said increase of pupation is within the range of 5 to 50%, such as within the range of 10 to 35%, such as within the range of 15 to 25%, such as within the range of 18 to 22%, such as around 20%.

105. Method according to any one of items 63 to 104, wherein said biomass comprises pupae of the family Pyralidae, and/or larvae of the family Pyralidae, and/or feces of said larvae.

106. Method according to item 105, wherein said biomass comprises pupae of the family Pyralidae.

107. Method according to item 105, wherein said biomass comprises larvae of the family Pyralidae.

108. Method according to item 105, wherein said biomass comprises feces of said larvae of the family Pyralidae.

109. Method according to items 107 to 46, wherein said biomass further comprises polyethylene glycol.

110. Method according to any one of items 63 to 109, wherein said biomass is harvested after at least 5 days, such as 10 days, such as 15 days, such as 16 days, such as 17 days, such as 18 days, such as 19 days, such as 20 days, such as 21 days, such as 22 days, such as 23 days, such as 24 days, such as 25 days, such as 30 days, such as 35 days, such as 40 days, such as 45 days.

111. Method for producing biomass according to any one of items 1-110, wherein said method is a continuous method, which method comprises the steps of
a) providing a population of larvae B,
b) bringing said population into contact with a feed as defined in any one of items 1 to 18, 20 to 21 and 23 to 37 and allowing said population to feed on said feed,
c) allowing an amount A of B to develop into pupae, and harvesting biomass comprising an amount (B-A) larvae,
d) allowing said pupae to transform into moths, and
e) allowing said moths to produce larvae, thereby obtaining a population of larvae B', and
repeating steps a) to e).

112. Method according to item 111, wherein said method does not require external addition of larvae.

113. Method according to any one of items 111 to 112, wherein said population of larvae B' is maintained at approximate ±1% of B, such as ±approximate 2% of B, such as ±approximate 3% of B, such as ±approximate 4% of B, such as ±approximate 5% of B, such as ±approximate 6% of B, such as ±approximate 7% of B, such as ±approximate 8% of B, such as ±approximate 9% of B, such as ±approximate 10% of B, such as ±approximate 11% of B, such as ±approximate 12% of B, such as ±approximate 13% of B, such as ±approximate 14% of B, such as ±approximate 15% of B, such as ±approximate 20% of B, such as ±approximate 25% of B.

114. Method according to any one of items 111 to 113, wherein said amount A is approximate 0.5% of B, such as approximate 1% of B, such as approximate 2% of B, such as approximate 3% of B, such as approximate 4% of B, such as approximate 5% of B, such as approximate 6% of B, such as approximate 7% of B, such as approximate 8% of B, such as approximate 9% of B, such as approximate 10% of B, such as approximate 11% of B, such as approximate 12% of B, such as approximate 13% of B, such as approximate 14% of B, such as approximate 15% of B, such as approximate 16% of B, such as approximate 17% of B, such as approximate 18% of B, such as approximate 19% of B, such as approximate 20% of B, such as approximate 25% of B, such as approximate 30% of B, such as approximate 35% of B, such as approximate 40% of B, such as approximate 45% of B, such as approximate 50% of B.

115. Method according to any one of items 63 to 114, wherein said at least one larva of the family Pyralidae is selected from the group consisting of *Galleria mellonella* and *Achroia grisella*.

116. Method according to any one items 63-114, wherein said at least one larva of the family Pyralidae is selected from the group consisting of *Galleria austrina*, *Galleria cerea*, *Galleria cerealis*, *Galleria cereana*, *Galleria cerella*, *Galleria crombrugghneela*, *Galleria obliquella*, and *Galleria mellonella*, such as wherein said at least one larva of the family Pyralidae is *Galleria mellonella*.

117. Method according any one of items 63 to 116, wherein said method is performed in a closed system.

118. Method according any one of items 63 to 117, wherein said larvae are brought into contact with said feed in a container.

119. Method according to item 119, wherein said container is made of glass, metals, metal alloys, composites, or treated wood, and any mixes thereof.

120. Method according any one of items 63 to 119, wherein said method is performed at a temperature of from 4° C. to 40° C., such as from 15° C. to 35° C., preferably of from 20° C. to 30° C., most preferably of from 25° C. to 27° C.

121. Method according any one of the items 63 to 120, wherein said method is performed at a humidity of from 30% to 99%.

122. Method according to item 121, wherein said humidity is maintained at 80.0+/−5%.

123. Method according any one of items 63 to 122, wherein said larva is subjected to starvation prior to adding any feed.

124. Method according to item 123, wherein said starvation is for 1 to 20 days, such as for 1 to 10, such as for 1 to 5 days, such as for 2 days.

The invention claimed is:

1. Method for producing biomass, the method comprising bringing at least one larva of the species *Galleria mellonella* into contact with a feed, wherein said feed comprises at least one plastic polymer, wherein said polymer is selected from the group consisting of polyethylene terephthalate, polyurethane, polyester, polyacrylate, polyglycol, polyvinyl chloride, polycarbonate, polyvinylidene chloride, synthetic polyamide, polypropylene terephthalate, polyether, poly(ethylene-vinylacetate), polyacrylonitrile, and mixes of distinct polymers or copolymers thereof;
allowing said at least one larva to feed on said at least one plastic polymer, thereby producing biomass; and wherein said method provides a suitable growth condition for a weight increase in said at least one larvae.

2. The method for producing biomass according to claim 1, wherein said feed consists of said at least one plastic polymer, wherein said polymer is selected from the group consisting of polyethylene terephthalate, polyurethane, polyester, polyacrylate, polyglycol, polyvinyl chloride, polycarbonate, polyvinylidene chloride, synthetic polyamide, polypropylene terephthalate, polyether, poly(ethylene-vinylacetate), polyacrylonitrile, and mixes of distinct polymers or copolymers thereof.

3. The method for producing biomass according to claim 1, wherein said polymer is selected from the group consisting of polyethylene terephthalate, polyurethane, polyester, polyacrylate, polyglycol, polyvinyl chloride, polycarbonate, polyvinylidene chloride, synthetic polyamide, and mixes of distinct polymers or copolymers thereof.

4. Method for increasing pupation in a population of larva of the species *Galleria mellonella*, the method comprising bringing said population of larva into contact with feed and allowing the population of larva to feed on said feed, wherein said feed comprises at least one polymer, wherein said polymer is selected from the group consisting of polyethylene, polyethylene terephthalate, polypropylene, polyurethane, polyester, polyacrylate, polyglycol, polyvinyl chloride, polycarbonate, polyvinylidene chloride, synthetic polyamide, polypropylene terephthalate, polyether, polystyrene, polysaccharide, poly(ethylene-vinylacetate), polyacrylonitrile, and mixes of distinct polymers or copolymers thereof; and wherein said pupation of larva fed under a suitable growth condition is increased compared to when a corresponding population of larva is fed a natural feed.

5. The method for increasing pupation according to claim 4, wherein said feed consists of at least one plastic polymer, wherein said polymer is selected from the group consisting of polyethylene, polyethylene terephthalate, polypropylene, polyurethane, polyester, polyacrylate, polyglycol, polyvinyl chloride, polycarbonate, polyvinylidene chloride, synthetic polyamide, polypropylene terephthalate, polyether, poly (ethylene-vinylacetate), polyacrylonitrile, and mixes of distinct polymers or copolymers thereof.

6. The method for increasing pupation according to claim 4, wherein said polymer is selected from the group consisting of polyethylene, polyethylene terephthalate, polypropylene, polyurethane, polyamide, polyester, polyacrylate, polystyrene, polyether, polyglycol, polysaccharide, polyvinyl chloride, polycarbonate, polyvinylidene chloride, and mixes of distinct polymers or copolymers thereof.

7. The method for increasing pupation according to claim 4, wherein said polymer is selected from the group consisting of synthetic polyamide; polyacrylate; a mixture of synthetic polyamide and a copolymer of polyether-polyurethane; polyethylene; polyester; cotton; and a mixture of polyester, synthetic polyamide and copolymer of polyether-polyurethane; and poly(ethylene-vinylacetate).

8. The method for increasing pupation according to claim 4, wherein said polymer is selected from the group consisting of synthetic polyamide; polyester; and poly(ethylene-vinylacetate).

* * * * *